(12) United States Patent
Flubacher et al.

(10) Patent No.: US 9,637,468 B2
(45) Date of Patent: May 2, 2017

(54) PROCESS FOR MANUFACTURING 5-(2,6-DI-4-MORPHOLINYL-4-PYRIMIDINYL)-4-TRIFLUORO-METHYLPYRIDIN-2-AMINE

(71) Applicants: Dietmar Flubacher, Bad Krozingen (DE); Nicole Bieri, Muttenz (CH); Murat Acemoglu, Basel (CH); Pascal Michel, Rheinfelden (CH); Rasmus Mose, Munich (DE); Hans Stettler, Allschwil (CH); Maria Caterina Testa, Basel (CH); Joerg Brozio, Basel (CH); Frank Schaefer, Rheinfelden (DE)

(72) Inventors: Dietmar Flubacher, Bad Krozingen (DE); Nicole Bieri, Muttenz (CH); Murat Acemoglu, Basel (CH); Pascal Michel, Rheinfelden (CH); Rasmus Mose, Munich (DE); Hans Stettler, Allschwil (CH); Maria Caterina Testa, Basel (CH); Joerg Brozio, Basel (CH); Frank Schaefer, Rheinfelden (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/437,177

(22) PCT Filed: Oct. 21, 2013

(86) PCT No.: PCT/EP2013/071996
§ 371 (c)(1),
(2) Date: Apr. 20, 2015

(87) PCT Pub. No.: WO2014/064058
PCT Pub. Date: May 1, 2014

(65) Prior Publication Data
US 2015/0246897 A1    Sep. 3, 2015

Related U.S. Application Data

(60) Provisional application No. 61/717,237, filed on Oct. 23, 2012, provisional application No. 61/842,101, filed on Jul. 2, 2013.

(51) Int. Cl.
| | | |
|---|---|---|
| C07D 401/04 | (2006.01) |
| C07D 213/75 | (2006.01) |
| C07F 5/02 | (2006.01) |
| C07D 413/14 | (2006.01) |
| A61K 31/5377 | (2006.01) |
| A61K 31/506 | (2006.01) |
| A61K 31/4433 | (2006.01) |
| A61K 31/444 | (2006.01) |
| C07D 401/14 | (2006.01) |
| C07D 239/28 | (2006.01) |
| C07D 239/42 | (2006.01) |

(52) U.S. Cl.
CPC ......... *C07D 401/04* (2013.01); *C07D 213/75* (2013.01); *C07D 239/28* (2013.01); *C07D 239/42* (2013.01); *C07D 401/14* (2013.01); *C07F 5/025* (2013.01)

(58) Field of Classification Search
CPC .. C07D 401/04; C07D 213/75; C07D 413/14; C07F 5/025; A61K 31/5377; A61K 31/506; A61K 31/4433; A61K 31/444
USPC ............ 544/82, 323; 546/13; 514/256, 275, 514/232.2, 340
See application file for complete search history.

(56) References Cited

FOREIGN PATENT DOCUMENTS

| | | | | |
|---|---|---|---|---|
| JP | 4061194 B2 | * | 3/2008 | ........... C07D 213/74 |
| WO | 2007/084786 A1 | | 7/2007 | |
| WO | 2012/044727 A2 | | 4/2012 | |
| WO | WO 2012044727 A2 | * | 4/2012 | ........... C07D 401/04 |

OTHER PUBLICATIONS

Wang et al., "Preparation and Diels-Alder/cross coupling reactions of a 2-diethanolaminoboron-substituted 1, 3-diene", Bielstein Journal of Organic Chemistry, 2009, vol. 5, No. 45, pp. 1-5.
Reilly et al., "DABO Boronates: Stable Heterocyclic Boronic Acid Complexes for Use in Suzuki-Miyaura Cross-Coupling Reactions", Synlett, 2011, No. 16, pp. 2392-2396.
Bonin et al., "Highly practical boronic acid surrogates for the Suzuki-Miyaura cross-coupling", Tetrahedron Letters, 2011, No. 52, pp. 1132-1135.

* cited by examiner

*Primary Examiner* — Alicia L Otton
*Assistant Examiner* — Sagar Patel
(74) *Attorney, Agent, or Firm* — Sandra Rueck

(57) ABSTRACT

The invention discloses improved processes for manufacturing a compound, 5-(2,6-Di-4-morpholinyl-4-pyrimidinyl)-4-trifluoromethylpyridin-2-amine, its monohydrochloride salt and intermediates thereof.

3 Claims, 5 Drawing Sheets

PROCESS FOR MANUFACTURING 5-(2,6-DI-4-MORPHOLINYL-4-PYRIMIDINYL)-4-TRIFLUORO-METHYLPYRIDIN-2-AMINE

FIELD OF THE INVENTION

The present invention relates to new, improved steps in manufacturing processes for pyrimidine derivatives, to intermediates thereof and to the manufacturing of intermediates. The present invention is directed to improved processes for manufacturing 5-(2,6-Di-4-morpholinyl-4-pyrimidinyl)-4-trifluoromethylpyridin-2-amine (Compound A, see below), the monohydrochloride salt of 5-(2,6-Di-4-morpholinyl-4-pyrimidinyl)-4-trifluoromethylpyridin-2-amine and intermediates thereof.

BACKGROUND OF THE INVENTION

WO 2007/084786 (priority date: Jan. 20, 2006) describes certain pyrimidine derivatives having phosphatidylinositol 3-kinase (hereinafter referred to as "PI3K") inhibiting properties, their use as pharmaceuticals and manufacturing processes thereof. One pyrimidine derivative disclosed in WO 2007/084786 is the selective phosphatidylinositol 3-kinase inhibitor compound 5-(2,6-Di-4-morpholinyl-4-pyrimidinyl)-4-trifluoromethylpyridin-2-amine, hereinafter referred to as "Compound A" or "the compound of formula A".

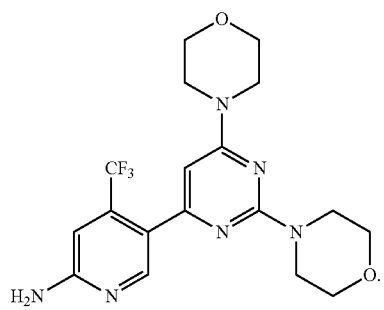

(A)

Compound A is described in WO 2007/084786 in free form and as the hydrochloric acid salt. The manufacturing process for preparing Compound A is described in Example 10 of this document. The manufacturing processes described therein are, although suitable for small scale production, regarded as disadvantageous for commercial production.

WO International Patent Application PCT/US2011/053808 discloses a process for manufacturing pyrimidine compounds, including Compound A, and their corresponding salts and polymorphs. The process of preparing compound A and the monohydrochloride salt is summarized in FIG. 1. The second step of the process that leads to the boronic acid or boronic ester is complicated, with yields ranging from 30-60%. The choice of the base required to react with the acidic proton of the amide is critical and requires 5 equivalents of lithium amide in addition to 2.5 equivalents of butyl lithium at low temperature for the the Li/Br exchange reaction. Additional complications arise from precipitation of the anion. Moreover the boronic acid is unstable at high pH (>9) and low pH (<1). The Suzuki coupling step is also complicated by the Pd catalyst required and removal of the Pd catalyst during work up. The salt forming step is also complicated, as addition of more than 1 equivalent of HCl results in formation of the monohydrochloride salt of 5-(2,6-Di-4-morpholinyl-4-pyrimidinyl)-4-trifluoromethylpyridin-2-amine along with amounts of the dihydrochloride salt of 5-(2,6-Di-4-morpholinyl-4-pyrimidinyl)-4-trifluoromethylpyridin-2-amine, the latter salt limiting the purity of the monohydrochloride salt.

There is a need for improved manufacturing methods of such compounds, especially where the purity of the intermediate compounds improve the purity of the active product ingredient, Compound A and its pharmaceutically acceptable salts. In particular there is a need to provide processes that fulfill one or more of the following criteria: scalable, safer; higher overall purity; higher yielding and more economical, as compared to the process disclosed.

SUMMARY OF THE INVENTION

Accordingly, the invention thus provides improved methods for manufacturing Compound A, which is summarized in FIGS. 2-5.

Accordingly, the invention provides a process for manufacturing a compound of formula A

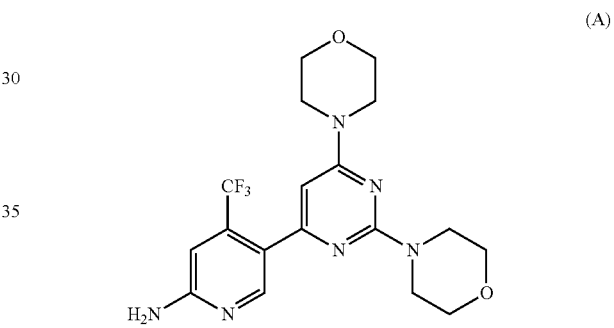

(A)

comprising the steps of:

(a) acylating 5-bromo-4-(trifluoromethyl)pyridin-2-amine to form N-(5-bromo-4-(trifluoromethyl)pyridin-2-yl)acetamide

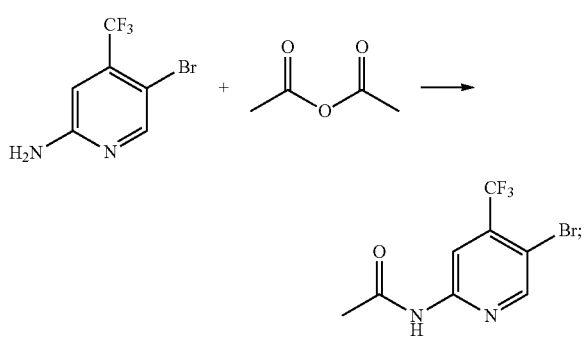

(b) reacting N-(5-bromo-4-(trifluoromethyl)pyridin-2-yl)acetamide with an alkyl Grignard reagent followed by an triaklylborate and 2,2'-azanediyldiethanol to form N-(5-(1,3,6,2-dioxazaborocan-2-yl)-4-(trifluoromethyl)pyridin-2-yl)acetamide

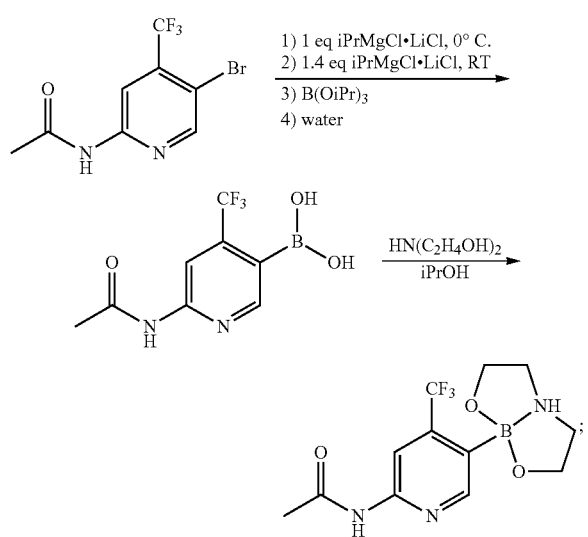

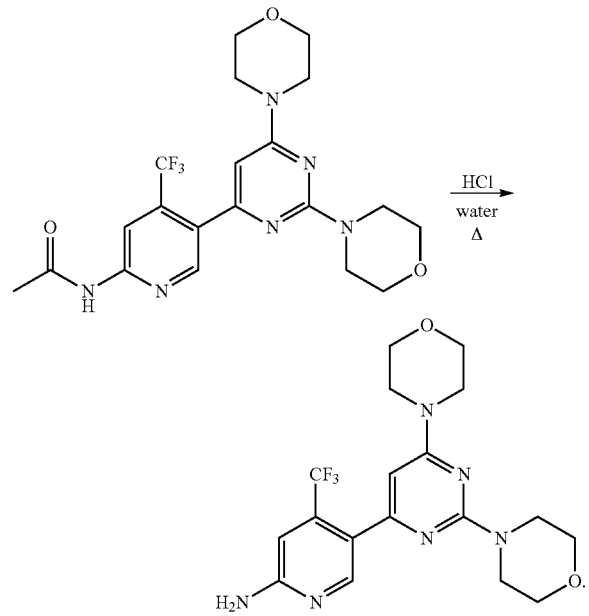

(c) coupling N-(5-(1,3,6,2-dioxazaborocan-2-yl)-4-(trifluoromethyl)pyridin-2-yl)acetamide with 4,4'-(6-Chloropyrimidine-2,4-diyl)di[morpholine] via a palladium catalyzed Suzuki reaction to form N-(5-(2,6-dimorpholinopyrimidin-4-yl)-4-(trifluoromethyl)pyridin-2-yl)acetamide

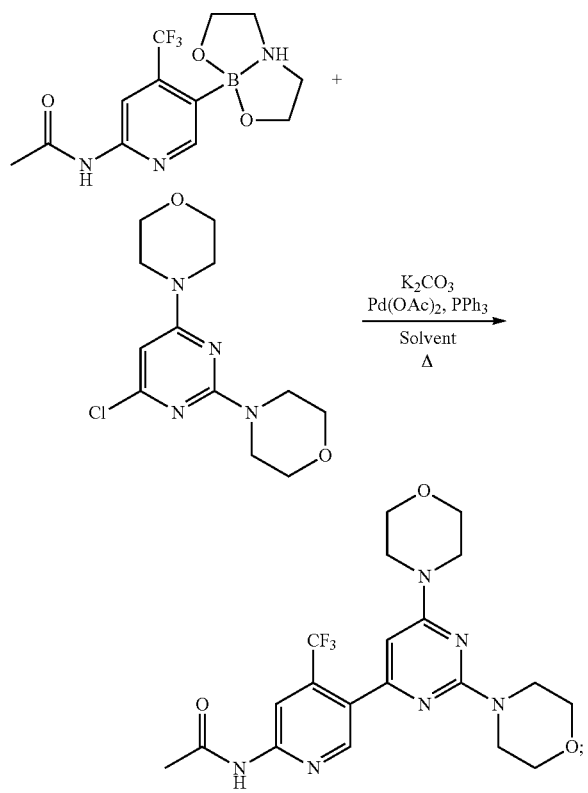

and (d) hydrolyzing N-(5-(2,6-dimorpholinopyrimidin-4-yl)-4-(trifluoromethyl)pyridin-2-yl)acetamide under acidic conditions to form the compound of formula A The invention also provides a process for manufacturing N-(5-(1,3,6,2-dioxazaborocan-2-yl)-4-(trifluoromethyl)pyridin-2-yl)acetamide comprising the steps of:

(a) reacting N-(5-bromo-4-(trifluoromethyl)pyridin-2-yl)acetamide with isopropylmagnesiumchloride, lithium chloride in tetrahydrofuran (b) adding tris(isopropylborate); and (c) further adding 2,2'-azanediyldiethanol

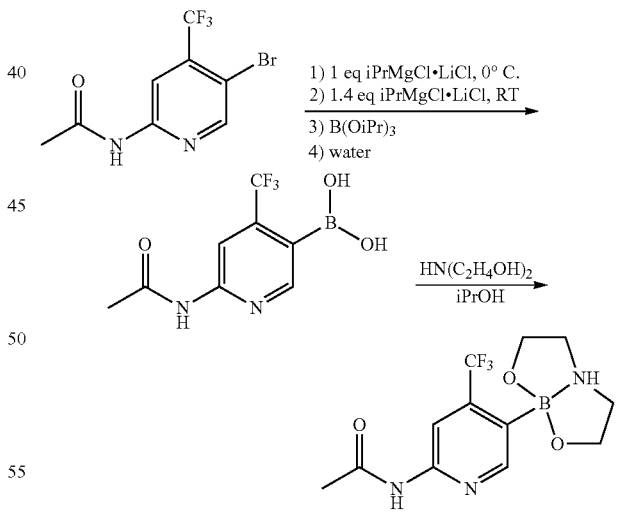

The invention also provides a process for manufacturing N-(5-(2,6-dimorpholinopyrimidin-4-yl)-4-(trifluoromethyl)pyridin-2-yl)acetamide comprising the step of coupling N-(5-(1,3,6,2-dioxazaborocan-2-yl)-4-(trifluoromethyl)pyridin-2-yl)acetamide and 4,4'-(6-Chloropyrimidine-2,4-diyl)di[morpholine] via a Suzuki coupling reaction wherein a palladium catalyst is generated in-situ using a mixture of Palladium(II) acetate, triphenylphosphine and an aqueous base

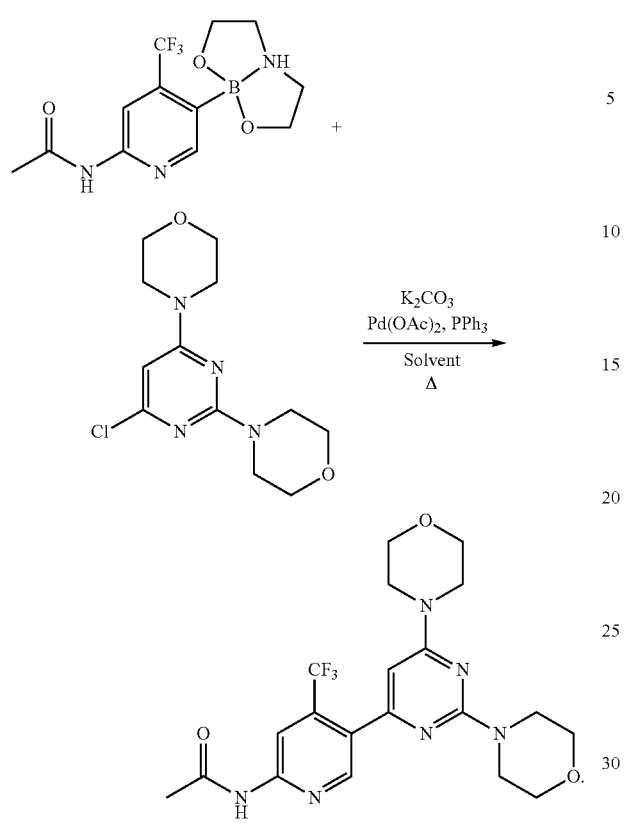

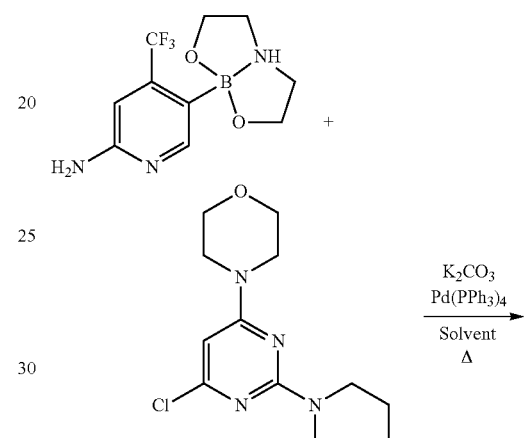

The invention also provides a process for manufacturing a compound of formula A (A)

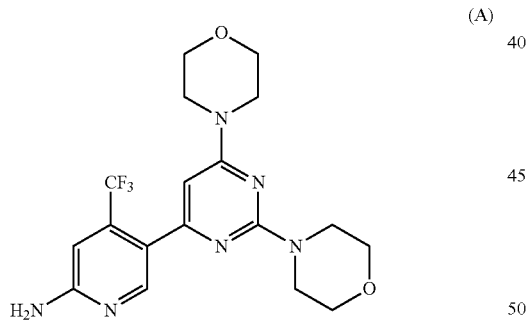

comprising the steps of:
(a) reacting a trianion of 5-bromo-4-(trifluoromethyl)pyridin-2-amine with an triaklylborate followed by 2,2'-azanediyldiethanol to form N-(5-(1,3,6,2-dioxaza-borocan-2-yl)-4-(trifluoromethyl)pyridin-2-yl)amine

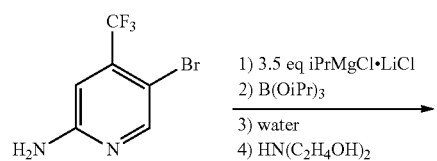

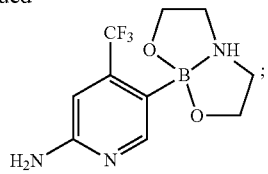

(b) coupling N-(5-(1,3,6,2-dioxazaborocan-2-yl)-4-(trifluoromethyl)pyridin-2-yl)amine with 4,4'-(6-Chloro-pyrimidine-2,4-diyl)di[morpholine] via a palladium catalyzed Suzuki coupling reaction to form the compound of formula A

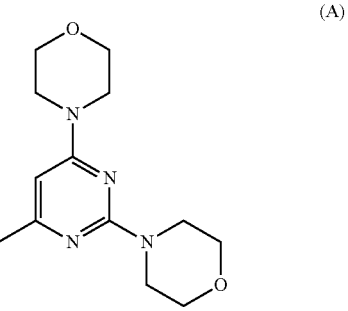

The invention also provides a process for manufacturing a compound of formula A (A)

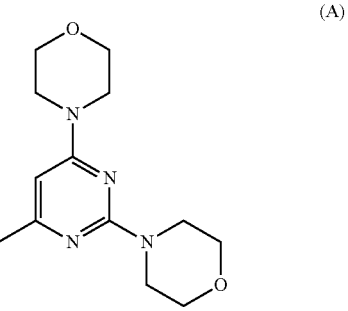

comprising the steps of:
(a) coupling a Grignard reagent prepared from the dianion N-(5-bromo-4-(trifluoromethyl)pyridin-2-yl)acetamide and 4,4'-(6-Chloropyrimidine-2,4-diyl)di[morpholine] via a metal catalyzed Kumada coupling reaction to form N-(5-(2,6-dimorpholinopyrimidin-4-yl)-4-(trifluoromethyl)pyridin-2-yl)acetamide and (b) hydrolyzing N-(5-(2,6-dimorpholinopyrimidin-4-yl)-4-(trifluoromethyl)pyridin-2-yl)acetamide under acidic conditions to form the compound of formula A The invention also provides a process for manufacturing a compound of formula A comprising the step of:

coupling a Grignard reagent prepared from the trianion of 5-bromo-4-(trifluoromethyl)pyridin-2-amine and 4,4'-(6-Chloropyrimidine-2,4-diyl)di[morpholine] via a metal catalyzed Kumada coupling reaction to form the compound of formula A

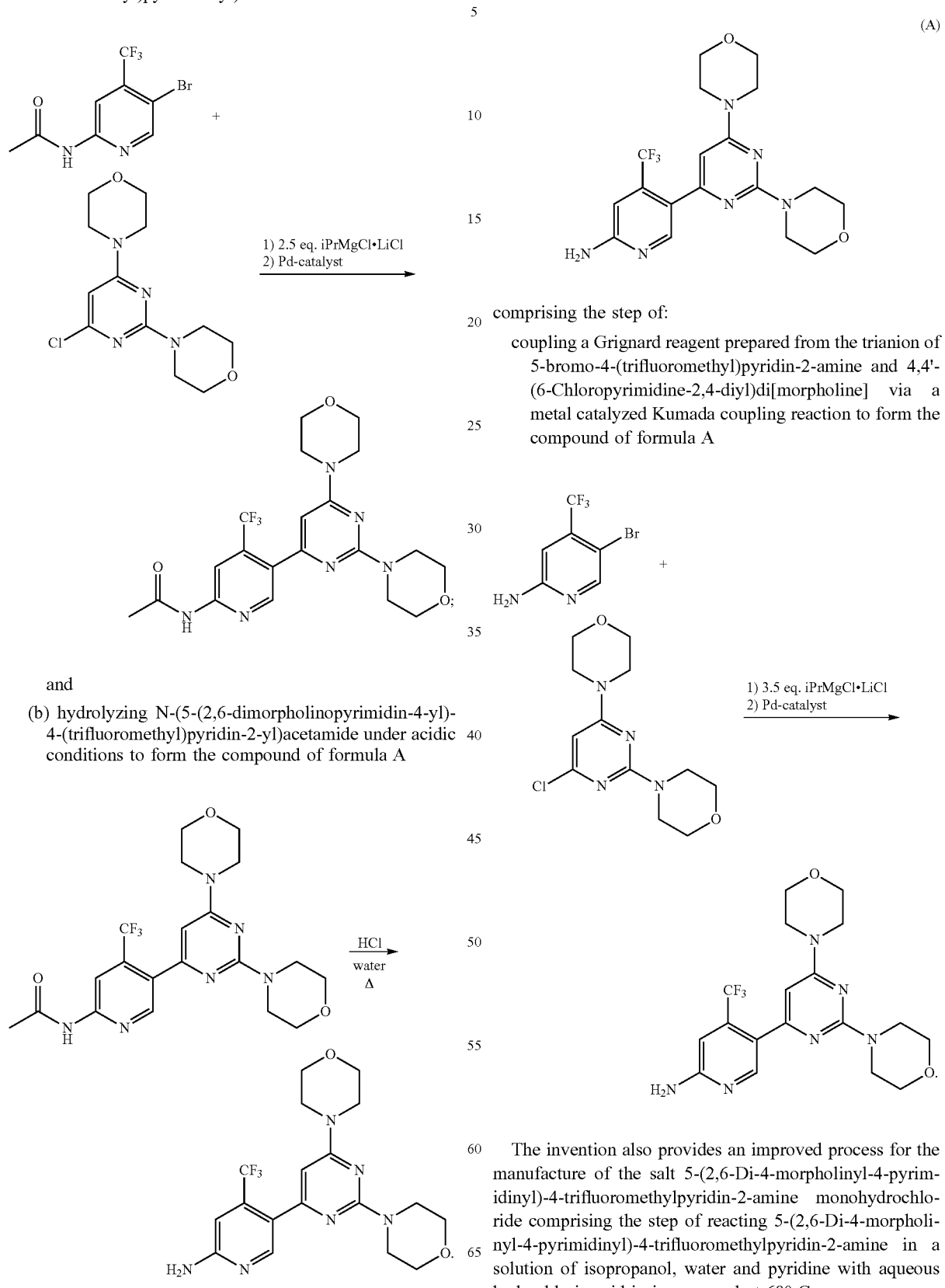

The invention also provides an improved process for the manufacture of the salt 5-(2,6-Di-4-morpholinyl-4-pyrimidinyl)-4-trifluoromethylpyridin-2-amine monohydrochloride comprising the step of reacting 5-(2,6-Di-4-morpholinyl-4-pyrimidinyl)-4-trifluoromethylpyridin-2-amine in a solution of isopropanol, water and pyridine with aqueous hydrochloric acid in isopropanol at 60° C.

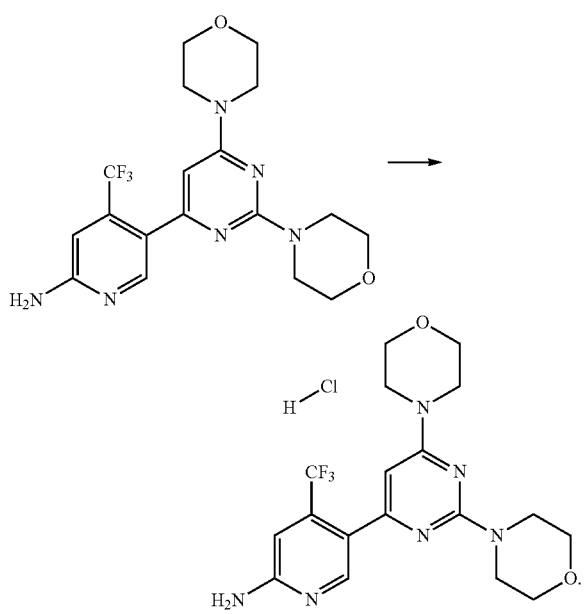

It was discovered that the improved manufacturing processes described herein, including the particular salt forming process step, fulfill one or more of the following criteria: safer; higher overall purity; higher yielding and more economical when compared to known processes for manufacturing 5-(2,6-Di-4-morpholinyl-4-pyrimidinyl)-4-trifluoromethylpyridin-2-amine and pharmaceutically acceptable salts thereof. Further, the manufacturing processes described herein are scalable, making them suitable for commercial production.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
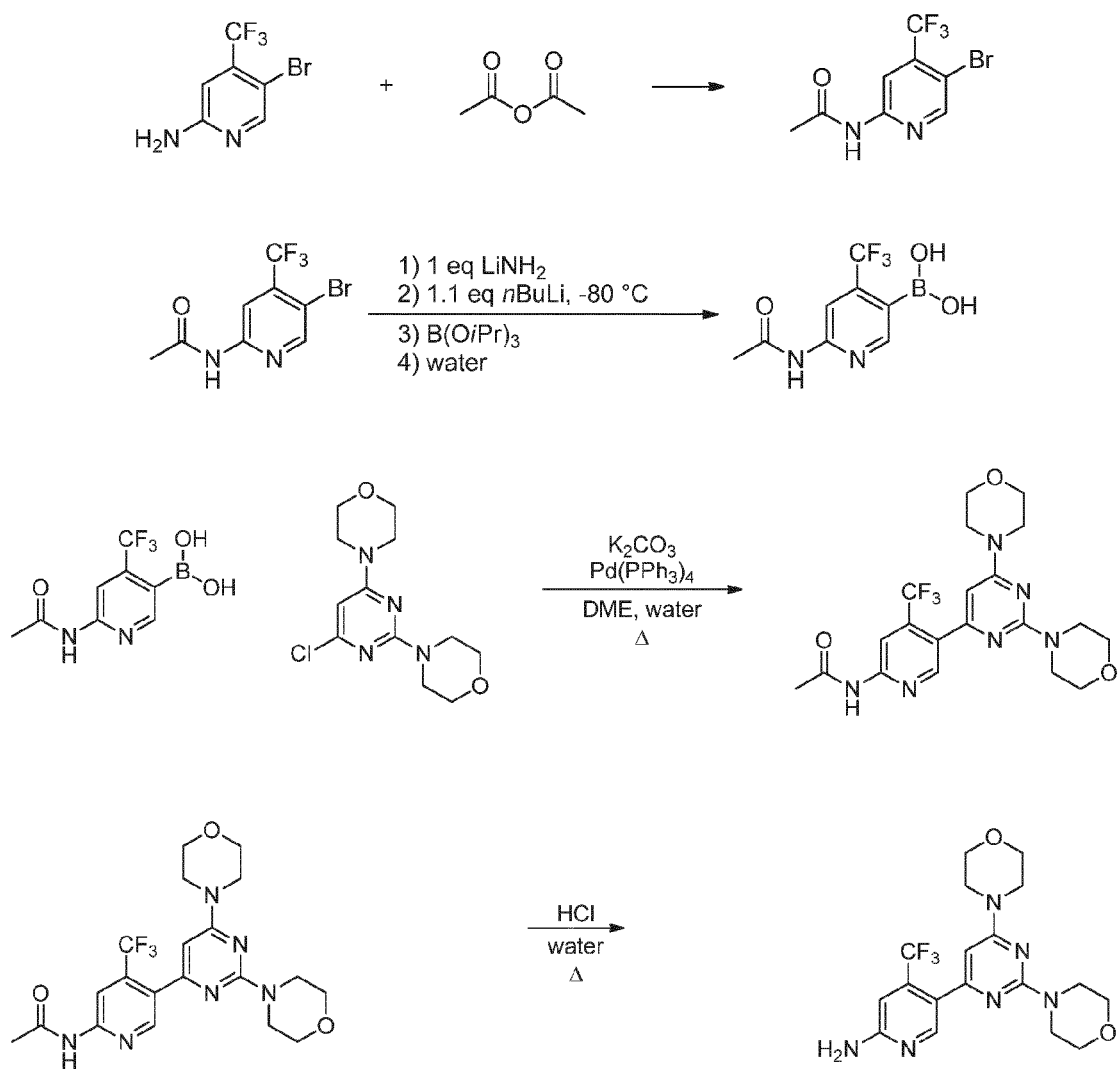
FIG. 1 outlines a process for manufacturing 5-(2,6-Di-4-morpholinyl-4-pyrimidinyl)-4-trifluoromethylpyridin-2-amine summarized in PCT/US2011/053808.

The compound 5-(2,6-Di-4-morpholinyl-4-pyrimidinyl)-4-trifluoromethylpyridin-2-amine is known to have PI3K inhibiting properties. Accordingly, the compound is valuable for the treatment of various diseases, in particular for the prophylaxis or treatment of proliferative diseases. Thus, there is a great need to provide improved manufacturing methods for 5-(2,6-Di-4-morpholinyl-4-pyrimidinyl)-4-trifluoromethylpyridin-2-amine and pharmaceutically acceptable salts thereof.

The invention will be better understood and objects other than those set forth above will become apparent when consideration is given to the following detailed description thereof, including the following glossary of terms, the concluding examples and the figures. The following general definitions shall apply in this specification, unless otherwise specified:

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New Jersey, (4$^{th}$ Edition, 2007) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

"Carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, alkyl esters, secondary amides and the like.

As used herein, the term "pharmaceutically acceptable salts" refers to the nontoxic acid or alkaline earth metal salts of the pyrimidine compounds of the invention. These salts can be prepared in situ during the final isolation and purification of the pyrimidine compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, pyridine hydrochloride, 2-hydroxyethanesulfonate, lactate, maleate, methane-sulfonate, nicotinate, 2-naphth-alenesulfonate, oxalate, pamoate, pectinate, persulfate, 3-phenylproionate, picrate, pivalate, propionate, succinate, sulfate, tartrate, thiocyanate, p-toluene-sulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Where the plural form (e.g., compounds, salts) is used, this includes the singular (e.g., a single compound, a single salt). "A compound" does not exclude that (e.g., in a pharmaceutical formulation) more than one compound of the formula A (or a salt thereof) is present.

Where the singular form (e.g., solvent, base) is used, this includes the plural (e.g., solvents, bases). "A solvent", "the solvent", "a base" or "the base" does not exclude that (e.g., in a reaction mixture) more than one solvent or base is present.

The salts of compounds of formula A are preferably pharmaceutically acceptable salts; such salts are known in the field.

Synthesis of 5-(2,6-Di-4-morpholinyl-4-pyrimidinyl)-4-trifluoromethylpyridin-2-amine (Compound A)

Figure 2:
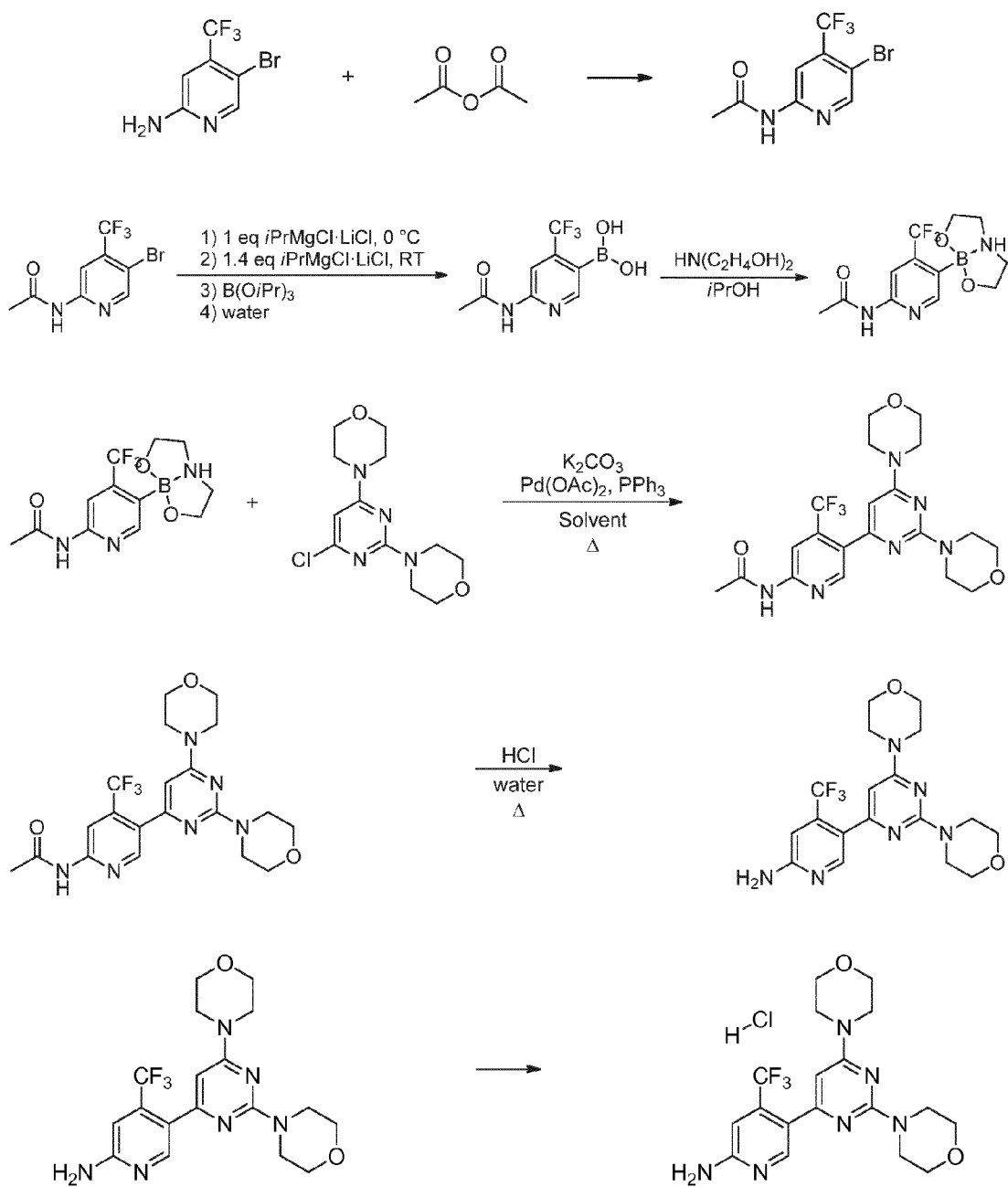
FIG. 2 summarizes one improved process for manufacturing 5-(2,6-Di-4-morpholinyl-4-pyrimidinyl)-4-trifluoromethylpyridin-2-amine.

Accordingly, one embodiment of invention provides an improved process, as summarized in FIG. 2, for manufacturing a compound of formula A (A)

comprising the steps of:
(a) acylating 5-bromo-4-(trifluoromethyl)pyridin-2-amine to form N-(5-bromo-4-(trifluoromethyl)pyridin-2-yl)acetamide (b) reacting N-(5-bromo-4-(trifluoromethyl)pyridin-2-yl)acetamide with an alkyl Grignard reagent followed by an triaklylborate and 2,2'-azanediyldiethanol to form N-(5-(1,3,6,2-dioxazaborocan-2-yl)-4-(trifluoromethyl)pyridin-2-yl)acetamide

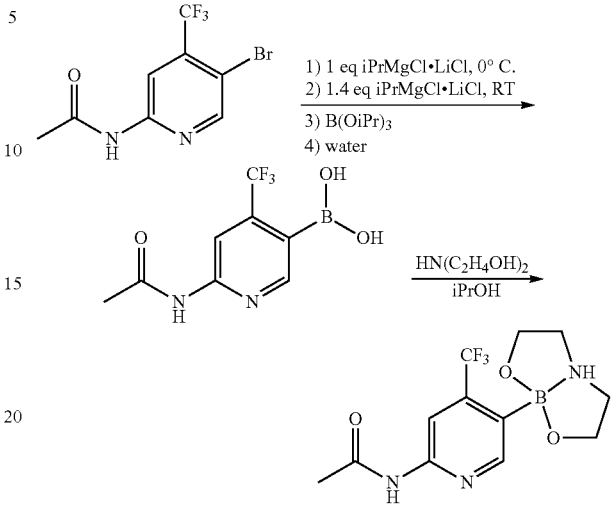

(c) coupling N-(5-(1,3,6,2-dioxazaborocan-2-yl)-4-(trifluoromethyl)pyridin-2-yl)acetamide with 4,4'-(6-Chloropyrimidine-2,4-diyl)di[morpholine] via a palladium catalyzed Suzuki coupling reaction to form N-(5-(2,6-dimorpholinopyrimidin-4-yl)-4-(trifluoromethyl)pyridin-2-yl)acetamide; and

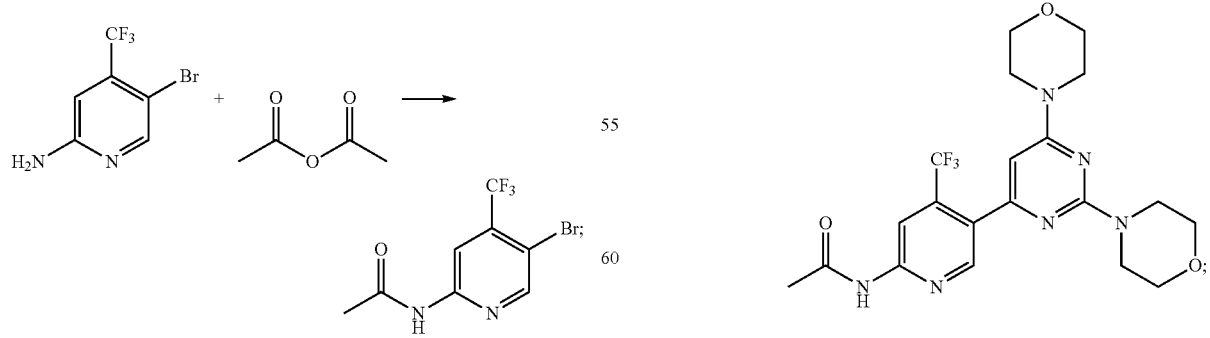

and
(d) hydrolyzing N-(5-(2,6-dimorpholinopyrimidin-4-yl)-4-(trifluoromethyl)pyridin-2-yl)acetamide under acidic conditions to form the compound of formula A.

Step (a)

In an exemplary embodiment, 5-bromo-4-(trifluoromethyl)pyridin-2-amine is acylated to form N-(5-bromo-4-(trifluoromethyl)pyridin-2-yl)acetamide in a reaction mixture comprising one or more solvents and an acid anhydride of formula $(R^5C{=}O)_2O$, such that $R^5$ is $C_{1-6}$ alkyl and phenyl. The one or more solvents are selected from aromatic solvents, aliphatic solvents, halogenated solvents, polar aprotic solvents, ester solvents and ethereal solvents. In one embodiment, the one or more solvents of step (a) comprises ethyl acetate and heptane and the acid anhydride is acetic anhydride. Typical reaction times are in the range of 4 to 8 hours. Typical reaction temperatures are in the range of 70° C. to 90° C. under reflux conditions. In one embodiment, acetic anhydride was continuously added within a time period of 3 hours and the reaction mixture was stirred at 80° C. for 5 hours. The one or more solvents are removed in vacuo and the product was precipitated by adding additional heptane and cooling. The product N-(5-bromo-4-(trifluoromethyl)pyridin-2-yl)acetamide was collected by filtration, dried under vacuum and used in step (b). Advantages of the improved process are that the solvent dimethylaminopyridine (DMAP), previously used as a solvent in step (a) of WO International Patent Application PCT/US2011/053808, is eliminated and that product purity is consistently high (>99%), coupled with product yields from 94-96%.

Step (b)

In an exemplary embodiment, N-(5-bromo-4-(trifluoromethyl)pyridin-2-yl)acetamide is reacted with an alkyl Grignard reagent, followed by adding a triaklylborate and by further adding 2,2'-azanediyldiethanol to form N-(5-(1,3,6,2-dioxazaborocan-2-yl)-4-(trifluoromethyl)pyridin-2-yl)acetamide in a reaction mixture comprising one or more solvents. The one or more solvents are selected from aromatic solvents, aliphatic solvents, and ethereal solvents. Typical alkyl Grignard reagents are selected from $C_{1-6}MgX$ (X is Cl, Br, I). Typical Grignard reagents are those that can be used to perform selective metalations, namely a Grignard reagent, salt complex. In one embodiment, the alkyl Grignard reagent is isopropylmagnesiumchloride, lithium chloride complex and the one or more solvents is tetrahydrofuran and the trialkylborate is triisopropylborate.

In one embodiment, the process of step (b) for manufacturing N-(5-(1,3,6,2-dioxazaborocan-2-yl)-4-(trifluoromethyl)pyridin-2-yl)acetamide further comprises the steps of:
(i) reacting N-(5-bromo-4-(trifluoromethyl)pyridin-2-yl) acetamide with isopropylmagnesiumchloride, lithium chloride in tetrahydrofuran;
(ii) adding triisopropylborate in one or more solvents; and
(iii) further adding 2,2'-azanediyldiethanol in one or more solvents.

Typical reaction temperatures for step (i) are in the range of 0° C. to 10° C. Advantages of using an alkyl Grignard reagent is that it functions as a selective base during deprotonation and produces a stable di-anion via the transmetalation reaction. The process has a further advantage over deprotonation/transmetalation using butyllithium at low temperatures in that the mono-anion does not precipitate and less equivalents of the alkyl Grignard reagent are employed as compared to the organolithium reagent for the bromide/metal exchange. Typical reaction temperatures for step (ii) are in the range of 10° C. to 30° C. In one embodiment, after the addition of triisopropylborate is complete, the tetrahydrofuran solvent is replaced with 2-methylterahydrofuran. Typical reaction temperatures for step (iii) are in the range of 0° C. to 30° C. In one embodiment, the one or more solvents are 2-methyltetrahydrofuran and isopropanol. The boronic ester product, N-(5-(1,3,6,2-dioxazaborocan-2-yl)-4-(trifluoromethyl)pyridin-2-yl)acetamide has several advantages over the boronic acid compound, including purity, yield and thermal stability as compared to the boronic acid.

Step (c)

In an exemplary embodiment, N-(5-(1,3,6,2-dioxazaborocan-2-yl)-4-(trifluoromethyl)pyridin-2-yl)acetamide is coupled with 4,4'-(6-Chloropyrimidine-2,4-diyl)di[morpholine] via a palladium catalyzed Suzuki reaction comprising a catalyst, a base and one or more solvents to form N-(5-(2,6-dimorpholinopyrimidin-4-yl)-4-(trifluoromethyl)pyridin-2-yl)acetamide.

The Suzuki reaction, which is utilized in many of the reactions described above, is, in principle, a known reaction in organic chemistry and denotes the palladium catalysed coupling of two reactants, wherein one of the reactants contains a reactive halide moiety and the other reactant contains a reactive boronic ester or boronic acid moiety. Suitable conditions for this reaction ("Suzuki conditions") are known to those of skill in the art and relate particularly to the choice of catalyst, of diluent, of further reaction aids, of reaction times and of reaction temperatures. This reaction was not yet applied using the particular starting materials as described herein, where it thus forms a new and inventive process. In a particular embodiment of the process, the Pd-catalyst is $Pd(PPh_3)_4$ is generated in-situ.

In one embodiment, the solvent of step (c) comprises one or more solvents selected from aromatic solvents, aliphatic solvents, halogenated solvents, polar aprotic solvents, ester solvents, ethereal solvents and water. In another embodiment, the solvent of step (c) comprises one or more solvents selected from dimethoxyethane, tetrahydrofuran, 1,4-dioxane, 2-methyltetrahydrofuran and water. In a particular embodiment, the solvent of step (c) comprises dimethoxyethane and water. In a further particular embodiment, the solvent of step (c) comprises tetrahydrofuran and water. The base of step (c) is selected from acetates, phosphates and carbonates. In a particular embodiment, the base of step (c) is potassium carbonate. The catalyst of step (c) comprises palladium. In certain embodiments, the catalyst is selected from tetrakis(triphenylphosphine)palladium(0) and bis(triphenylphosphine)palladium (II) dichloride. In other embodiments, the palladium catalyst of step (c) is formed by combining $Pd(OAc)_2$ with a phosphine ligand. Suitable phosphine ligands are known to those of skill in the art; non-limiting examples include triphenylphosphine and tris(4-methoxy-3,5-dimethylphenyl)phosphine. In a particular embodiment, the catalyst of step (c) is tetrakis(triphenylphosphine)palladium(0). Suitable amounts of catalyst are in the range of 0.1 to 20 mol % to preferably 1 to 10 mol %. Typical reaction times are in the range of 1 min to 2 days, preferably 10 min to 10 hrs, particular preferably 1 to 3 hours. Typical reaction temperatures are in the range of 20° C. to reflux conditions, preferably 30° C. to 90° C. particular preferably 40-60° C.

In a further advantageous embodiment, the invention relates to a process according to process step (c) wherein the work up of the initially obtained reaction mixture comprises the steps of i) separating insoluble material (e.g., by filtering the insolubles, preferably by filtration using a filtration aid such as a celite pad), ii) separating the organic phase, and optionally replacing the solvent by another solvent (such as isopropyl acetate) iii) removing the residual palladium, and iv) crystallizing the product (preferably after aqueous acid extraction and pH controlled precipitation).

Advantages of the invention are the Suzuki catalyst can be generated in-situ and that product purification and palladium catalyst removal is carried out using extraction, with no handling of solids. Additional advantages are that steps (c) and (d) can be combined as a single process step.

Step (d)

In an exemplary embodiment, N-(5-(2,6-dimorpholinopyrimidin-4-yl)-4-(trifluoromethyl)pyridin-2-yl)acetamide is hydrolyzed in one or more solvents under acidic conditions to form the compound of formula A.

In one embodiment, the solvent of step (d) comprises one or more solvents selected from aromatic solvents, aliphatic solvents, halogenated solvents, polar aprotic solvents, ester solvents, ethereal solvents and water. In a particular embodiment, the one or more solvents of step (d) is water. In another particular embodiment, the one or more solvents of step (d) is water and isopropylacetate.

In step (d), removal of the acetyl moiety also entails replacement of this moiety with a hydrogen atom. Removal of the acetyl moiety can be performed by methods known to those of skill in the art. Non-limiting examples of such methods include acid-, base- and metal-mediated reactions. A particular example of such methods is acid-mediated hydrolysis. In one embodiment of step (d), the reagent for the removal of the acetyl moiety is selected from acids, bases and metal catalysts. In a particular embodiment of step (d), the reagent for the removal of the acetyl moiety is hydrochloric acid.

In certain embodiments, steps (a)-(d) independently comprise additional steps or procedures (e.g., to remove reaction byproducts, or to workup, isolate or purify reaction products) as detailed in the examples herein.

In certain embodiments, steps (a)-(d) is followed by salt formation.

The skilled practitioner will recognize several parameters of the foregoing processes that may be varied advantageously in order to obtain a desirable outcome. These parameters include, for example, the methods and means of purification of reaction components and solvents; the order of addition of said reaction components and solvents to the reaction mixture; the duration of reaction of said reaction components and solvents; and the temperature and rate of stirring, mixing or agitation of the reaction components and solvents during said reaction.

It was found that the process embodied by steps (a)-(d) (also including the particular process steps) fulfills one or more of the following criteria: safer; simpler; higher yielding and more economical when compared to known processes for manufacturing the compound of formula A. Further, the process as described herein is considered scalable, making it suitable for commercial production.

Alternative Synthesis of 5-(2,6-Di-4-morpholinyl-4-pyrimidinyl)-4-trifluoromethylpyridin-2-amine (Compound A)

Figure 3:
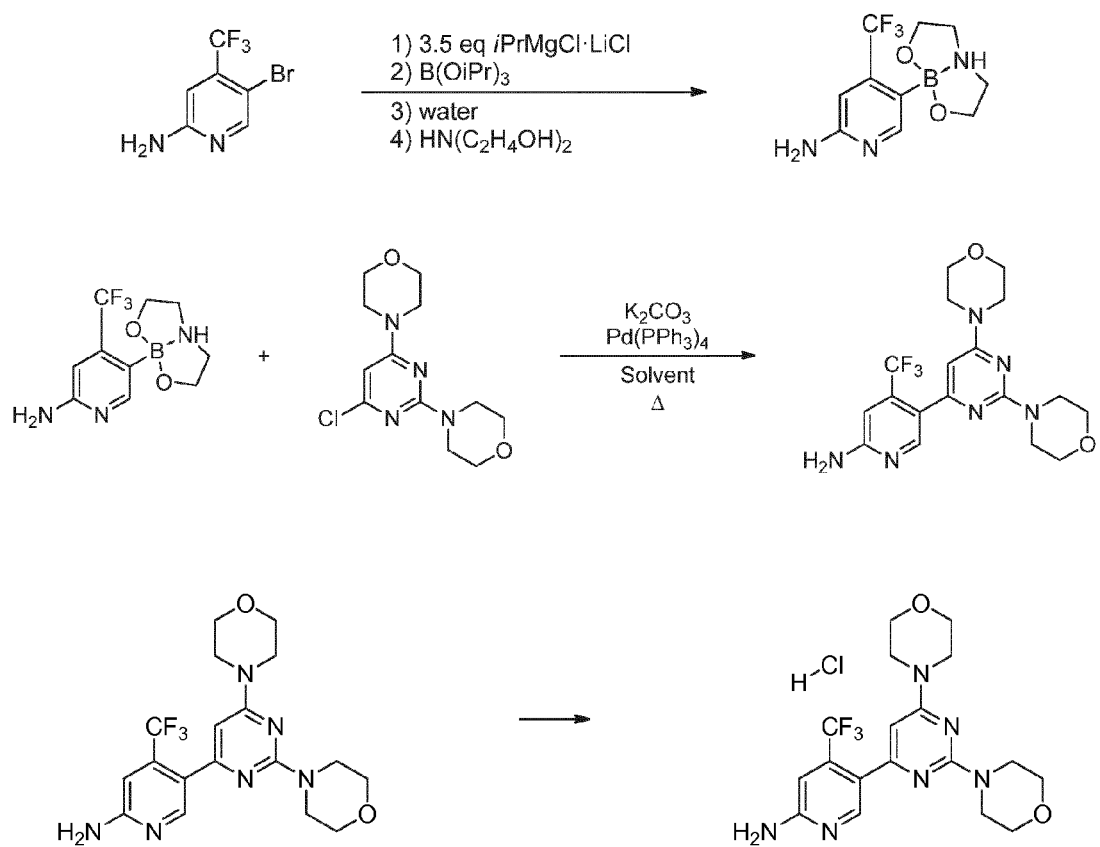
FIG. 3 summarizes an alternative improved process for manufacturing 5-(2,6-Di-4-morpholinyl-4-pyrimidinyl)-4-trifluoromethylpyridin-2-amine.

The invention also provides an alternative process (FIG. 3) for manufacturing a compound of formula A

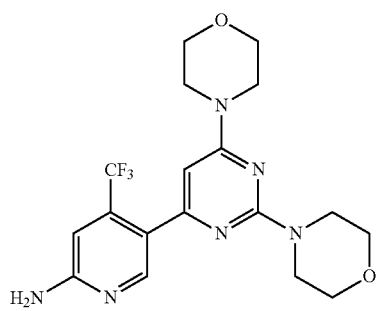

(A)

comprising the steps of:
(a) reacting 5-bromo-4-(trifluoromethyl)pyridin-2-amine with an alkyl Grignard reagent followed by an triaklylborate and 2,2'-azanediyldiethanol to form N-(5-(1,3,6,2-dioxazaborocan-2-yl)-4-(trifluoromethyl)pyridin-2-yl)amine

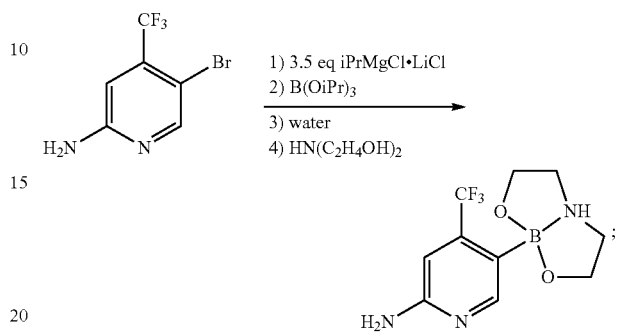

(b) coupling N-(5-(1,3,6,2-dioxazaborocan-2-yl)-4-(trifluoromethyl)pyridin-2-yl)amine with 4,4'-(6-Chloropyrimidine-2,4-diyl)di[morpholine] via a palladium catalyzed Suzuki coupling reaction to form the compound of formula A

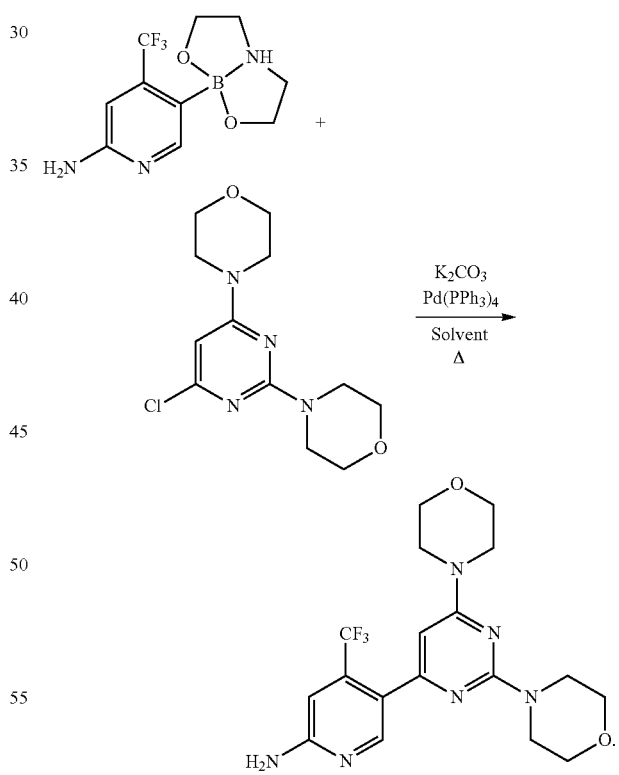

Step (a)

In an exemplary embodiment, 5-bromo-4-(trifluoromethyl)pyridin-2-amine is reacted with 3.5 equivalents of an alkyl Grignard reagent, followed by adding a triaklylborate and by further adding 2,2'-azanediyldiethanol to form N-(5-(1,3,6,2-dioxazaborocan-2-yl)-4-(trifluoromethyl)pyridin-2-yl)amine in a reaction mixture comprising one or more solvents. The one or more solvents are selected from aromatic solvents, aliphatic solvents, and ethereal solvents. Typical alkyl Grignard reagents are selected from $C_{1-6}MgX$ (X is Cl, Br, I). Typical Grignard reagents are those that can be used to perform selective metalations, namely a Grignard reagent, salt complex. In one embodiment, the alkyl Grignard reagent is isopropylmagnesiumchloride, lithium chloride complex and the one or more solvents is tetrahydrofuran and the trialkylborate is triisopropylborate.

Step (b)

In an exemplary embodiment, N-(5-(1,3,6,2-dioxazaborocan-2-yl)-4-(trifluoromethyl)pyridin-2-yl)amine is coupled with 4,4'-(6-Chloropyrimidine-2,4-diyl)di[morpholine] via a palladium catalyzed Suzuki reaction comprising a catalyst, a base and one or more solvents to form 5-(2,6-Di-4-morpholinyl-4-pyrimidinyl)-4-trifluoromethylpyridin-2-amine (Compound A).

The Suzuki reaction, which is utilized in many of the reactions described above, is, in principle, a known reaction in organic chemistry and denotes the palladium catalysed coupling of two reactants, wherein one of the reactants contains a reactive halide moiety and the other reactant contains a reactive boronic ester or boronic acid moiety. Suitable conditions for this reaction ("Suzuki conditions") are known to those of skill in the art and relate particularly to the choice of catalyst, of diluent, of further reaction aids, of reaction times and of reaction temperatures. This reaction was not yet applied using the particular starting materials as described herein, where it thus forms a new and inventive process. In one embodiment of the process, the Pd-catalyst is $Pd(PPh_3)_4$. In another embodiment of the process, the Pd-catalyst is $Pd(PPh_3)_4$ is generated in-situ.

In one embodiment, the solvent of step (b) comprises one or more solvents selected from aromatic solvents, aliphatic solvents, halogenated solvents, polar aprotic solvents, ester solvents, ethereal solvents and water. In another embodiment, the solvent of step (b) comprises one or more solvents selected from dimethoxyethane, tetrahydrofuran, 1,4-dioxane, 2-methyltetrahydrofuran and water. The base of step (b) is selected from acetates, phosphates and carbonates. In a particular embodiment, the base of step (b) is potassium carbonate. The catalyst of step (b) comprises palladium. In certain embodiments, the catalyst is selected from tetrakis(triphenylphosphine)palladium (0) and bis(triphenylphosphine)palladium (II) dichloride. In other embodiments, the palladium catalyst of step (b) is formed by combining $Pd(OAc)_2$ with a phosphine ligand. Suitable phosphine ligands are known to those of skill in the art; non-limiting examples include triphenylphosphine and tris(4-methoxy-3,5-dimethylphenyl)phosphine. In a particular embodiment, the catalyst of step (b) is tetrakis(triphenylphosphine)palladium(0). Suitable amounts of catalyst are in the range of 0.1 to 20 mol % to preferably 1 to 10 mol %. Typical reaction times are in the range of 1 min to 2 days, preferably 10 min to 10 hrs, particular preferably 1 to 3 hours. Typical reaction temperatures are in the range of 20° C. to reflux conditions, preferably 30° C. to 90° C. particular preferably 40-60° C.

In one embodiment, steps (a) and (b) can be combined as a single step.

Alternative Synthesis of 5-(2,6-Di-4-morpholinyl-4-pyrimidinyl)-4-trifluoromethylpyridin-2-amine (Compound A)

Figure 4:
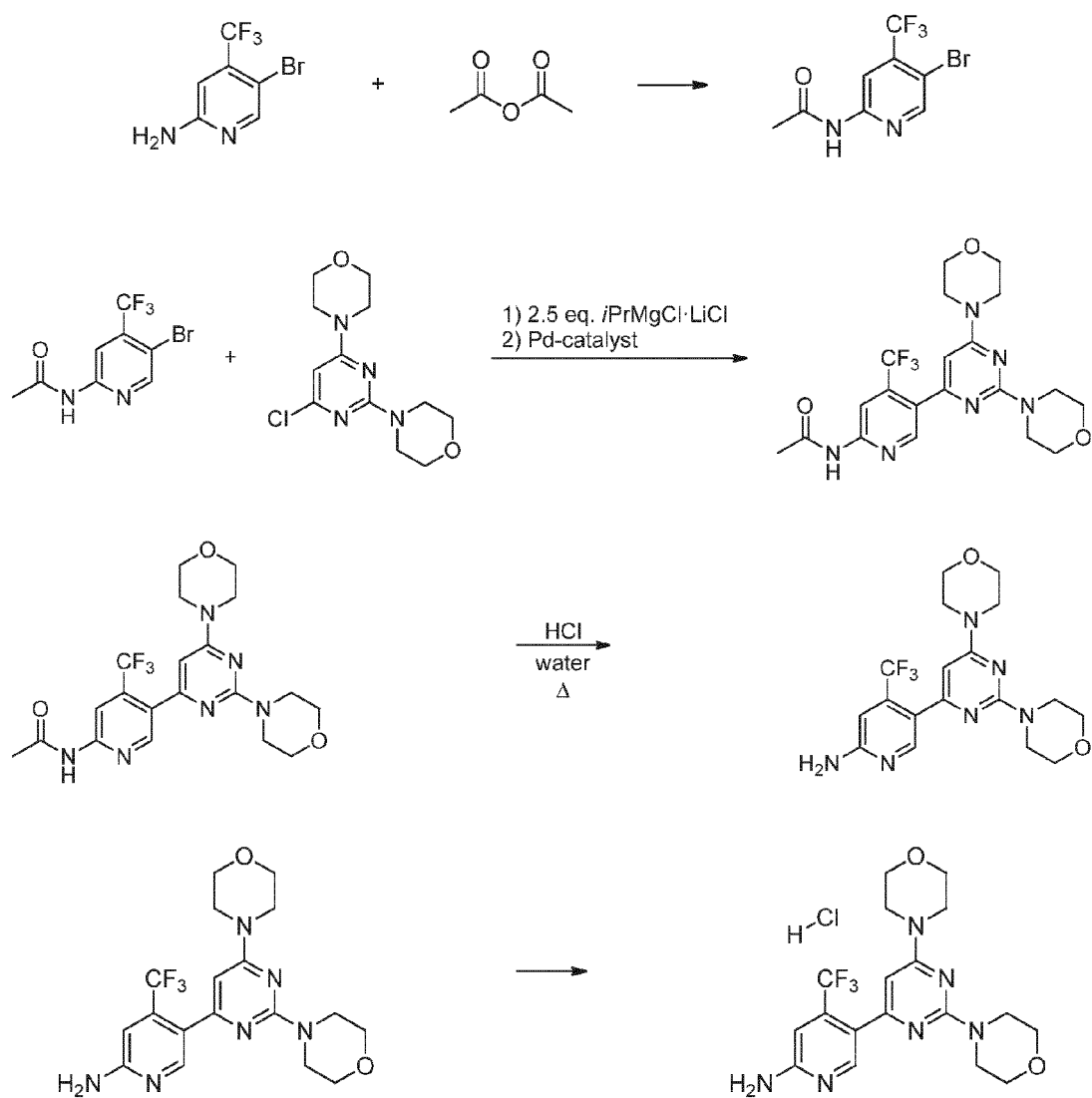
FIG. 4 summarizes an alternative improved process for manufacturing 5-(2,6-Di-4-morpholinyl-4-pyrimidinyl)-4-trifluoromethylpyridin-2-amine.

The invention also provides an alternative process (FIG. 4) for manufacturing a compound of formula A

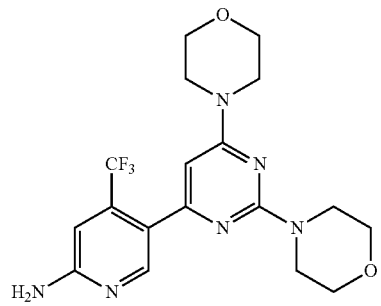

comprising the steps of:

(a) coupling a dianion N-(5-bromo-4-(trifluoromethyl)pyridin-2-yl)acetamide and 4,4'-(6-Chloropyrimidine-2,4-diyl)di[morpholine] via a palladium catalyzed Kumada coupling reaction to form N-(5-(2,6-dimorpholinopyrimidin-4-yl)-4-(trifluoromethyl)pyridin-2-yl)acetamide

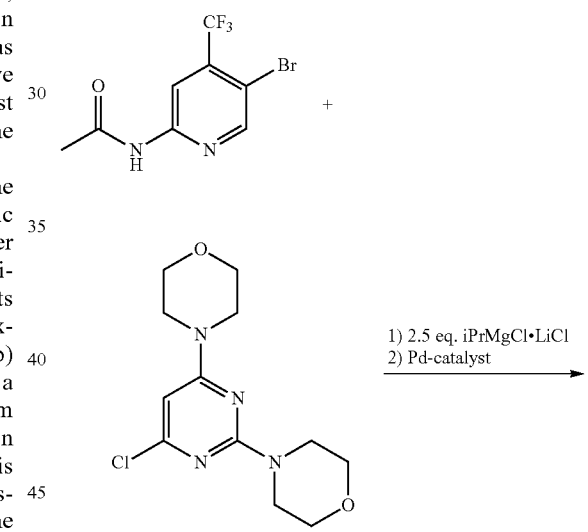

and (b) hydrolyzing N-(5-(2,6-dimorpholinopyrimidin-4-yl)-4-(trifluoromethyl)pyridin-2-yl)acetamide under acidic conditions to form the compound of formula A

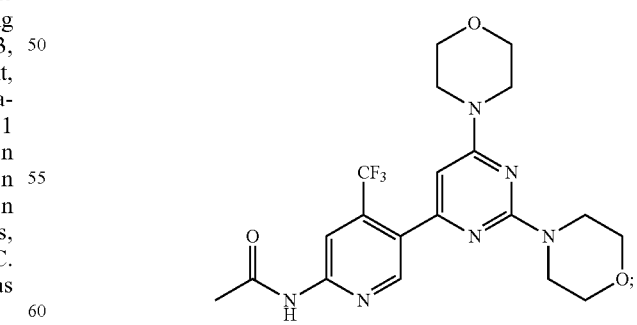

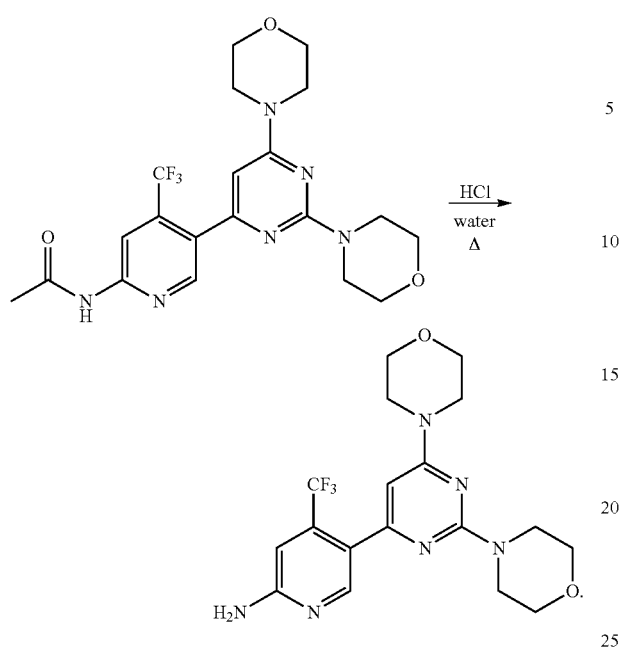

Step (a)

In an exemplary embodiment, N-(5-bromo-4-(trifluoromethyl)pyridin-2-yl)acetamide is reacted with 2.5 equivalents of an alkyl Grignard reagent in a reaction mixture comprising one or more solvents to form the Grignard reagent that is the dianion of N-(5-bromo-4-(trifluoromethyl)pyridin-2-yl)acetamide. The one or more solvents are selected from aromatic solvents, aliphatic solvents, and ethereal solvents. Typical alkyl Grignard reagents are selected from $C_{1-6}MgX$ (X is Cl, Br, I). Typical Grignard reagents are those that can be used to perform selective metalations, namely a Grignard reagent, salt complex. In one embodiment, the alkyl Grignard reagent is isopropylmagnesiumchloride, lithium chloride complex and the one or more solvents is tetrahydrofuran. The Kumada reaction, which is utilized in many of the reactions described above, is, in principle, a known reaction in organic chemistry and denotes the palladium or nickel catalysed carbon-carbon coupling of two reactants, wherein one of the reactants contains a reactive halide moiety and the other reactant contains a reactive Grignard reagent. Suitable conditions for this reaction ("Kumada conditions") are known to those of skill in the art and relate particularly to the choice of catalyst, of diluent, of further reaction aids, of reaction times and of reaction temperatures. This reaction was not yet applied using the particular starting materials as described herein, where it thus forms a new and inventive process. In one embodiment of the process, the Pd-catalyst is $Pd(acetate)_2$ and 1,1'-Bis(diphenylphosphino)ferrocene. In another embodiment of the process, the Pd-catalyst is $NiCl_2(dppf)$.

In one embodiment, the solvent of step (a) comprises one or more solvents selected from ethereal solvents and water. In another embodiment, the solvent of step (a) comprises one or more solvents selected from dimethoxyethane, tetrahydrofuran, 1,4-dioxane, 2-methyltetrahydrofuran and water. In other embodiments, the palladium catalyst of step (a) is formed by combining $Pd(OAc)_2$ with a phosphine ligand. Suitable phosphine ligands are known to those of skill in the art; non-limiting examples include triphenylphosphine and 1,1'-Bis(diphenylphosphino)ferrocene. Suitable amounts of catalyst are in the range of 0.1 to 20 mol % to preferably 1 to 10 mol %. Typical reaction times are in the range of 1 min to 2 days, preferably 10 min to 10 hrs, particular preferably 1 to 3 hours. Typical reaction temperatures are in the range of 20° C. to reflux conditions, preferably 30° C. to 90° C. particular preferably 40-60° C.

Alternative Synthesis of 5-(2,6-Di-4-morpholinyl-4-pyrimidinyl)-4-trifluoromethylpyridin-2-amine (Compound A)

Figure 5:
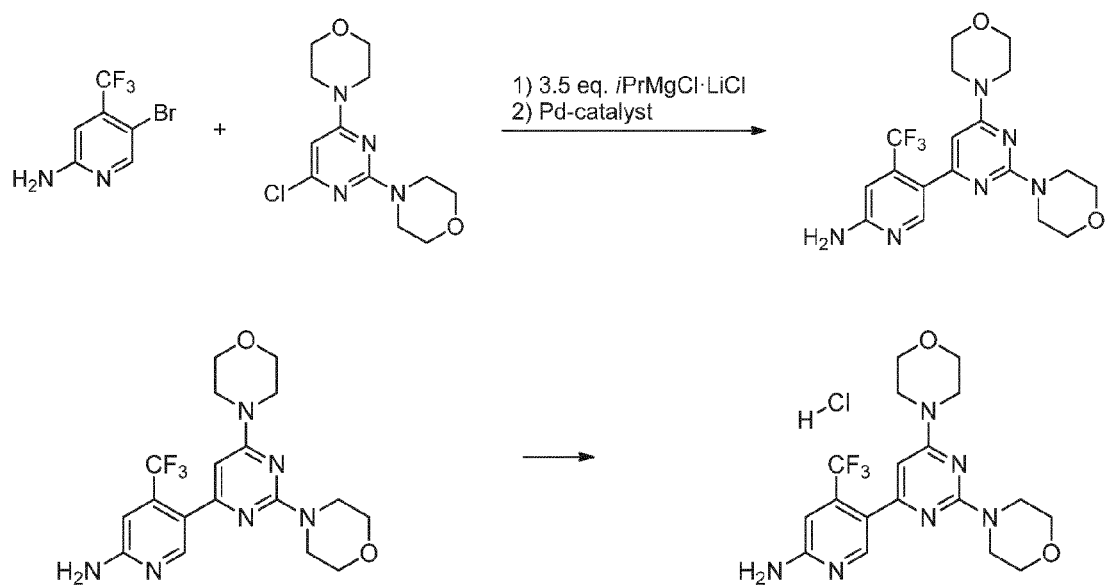
FIG. 5 summarizes an alternative improved process for manufacturing 5-(2,6-Di-4-morpholinyl-4-pyrimidinyl)-4-trifluoromethylpyridin-2-amine.

The invention also provides an alternative process (FIG. 5) for manufacturing a compound of formula A

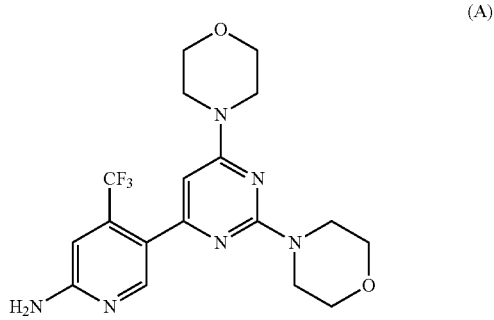 [SMILES: Nc1cc(C(F)(F)F)c(-c2cc(N3CCOCC3)nc(N3CCOCC3)n2)cn1]

comprising the step of:
coupling a trianion of 5-bromo-4-(trifluoromethyl)pyridin-2-amine with 4,4'-(6-Chloropyrimidine-2,4-diyl)di[morpholine] via a palladium catalyzed Kumada coupling reaction to form the compound of formula A

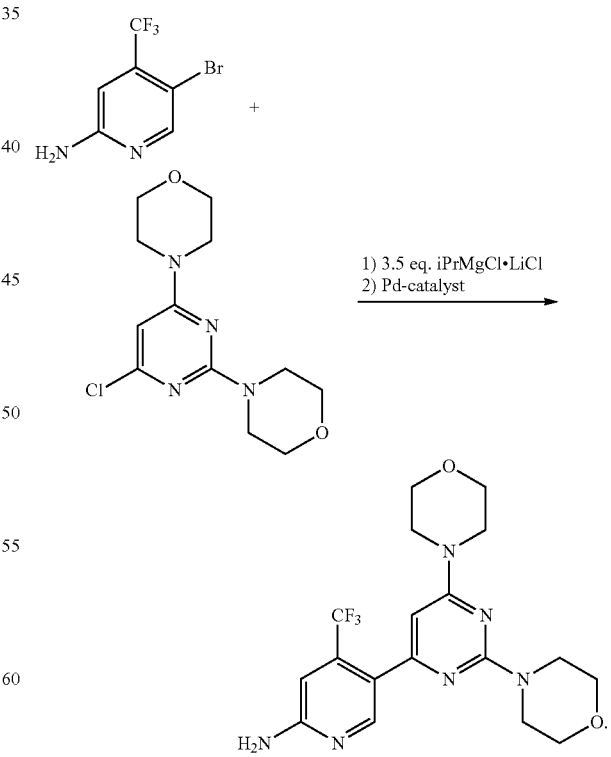

In an exemplary embodiment, N-(5-bromo-4-(trifluoromethyl)pyridin-2-yl)amine is reacted with 3.5 equivalents of an alkyl Grignard reagent in a reaction mixture comprising one or more solvents to form a Grignard reagent that the trianion of N-(5-bromo-4-(trifluoromethyl)pyridin-2-yl) amine. The one or more solvents are selected from aromatic solvents, aliphatic solvents, and ethereal solvents. Typical alkyl Grignard reagents are selected from $C_{1-6}MgX$ (X is Cl, Br, I).

Typical Grignard reagents are those that can be used to perform selective metalations, namely a Grignard reagent, salt complex. In one embodiment, the alkyl Grignard reagent is isopropylmagnesiumchloride, lithium chloride complex and the one or more solvents is tetrahydrofuran. The Kumada reaction, which is utilized in many of the reactions described above, is, in principle, a known reaction in organic chemistry and denotes the palladium or nickel catalysed carbon-carbon coupling of two reactants, wherein one of the reactants contains a reactive halide moiety and the other reactant contains a reactive Grignard reagent. Suitable conditions for this reaction ("Kumada conditions") are known to those of skill in the art and relate particularly to the choice of catalyst, of diluent, of further reaction aids, of reaction times and of reaction temperatures. This reaction was not yet applied using the particular starting materials as described herein, where it thus forms a new and inventive process. In one embodiment of the process, the Pd-catalyst is Pd(acetate)$_2$ and 1,1'-Bis(diphenylphosphino)ferrocene. In another embodiment of the process, the Pd-catalyst is $NiCl_2$ (dppf).

In one embodiment, the solvent of step (a) comprises one or more solvents selected from ethereal solvents and water. In another embodiment, the solvent of step (a) comprises one or more solvents selected from dimethoxyethane, tetrahydrofuran, 1,4-dioxane, 2-methyltetrahydrofuran and water. In other embodiments, the palladium catalyst of step (a) is formed by combining $Pd(OAc)_2$ with a phosphine ligand. Suitable phosphine ligands are known to those of skill in the art; non-limiting examples include triphenylphosphine and 1,1'-Bis(diphenylphosphino)ferrocene. Suitable amounts of catalyst are in the range of 0.1 to 20 mol % to preferably 1 to 10 mol %. Typical reaction times are in the range of 1 min to 2 days, preferably 10 min to 10 hrs, particular preferably 1 to 3 hours. Typical reaction temperatures are in the range of 20° C. to reflux conditions, preferably 30° C. to 90° C. particular preferably 40-60° C.

Improved Process for Manufacturing Monohydrochloride Salt of 5-(2,6-Di-4-morpholinyl-4-pyrimidinyl)-4-trifluoromethylpyridin-2-amine An improved process for forming the monohydrochloride salt of 5-(2,6-Di-4-morpholinyl-4-pyrimidinyl)-4-trifluoromethylpyridin-2-amine as crystalline form A was discovered. Aqueous hydrochloric acid (in amounts from less than one, e.g. 0.94 to over one equivalent, e.g. 1.1 equivalents) in alcoholic solution in the presence of pyridine at elevated temperature when added to 1 equivalent of 5-(2,6-Di-4-morpholinyl-4-pyrimidinyl)-4-trifluoromethylpyridin-2-amine provides the monohydrochloride salt of 5-(2,6-Di-4-morpholinyl-4-pyrimidinyl)-4-trifluoromethylpyridin-2-amine as crystalline form A, in high purity, with no impurities from the dihydrochloride salt of 5-(2,6-Di-4-morpholinyl-4-pyrimidinyl)-4-trifluoromethylpyridin-2-amine. Pyridine functions to buffer amounts of HCl more than one equivalent so that a monohydrochloride salt is formed. Pyridinehydrochloride acid salt (less than 1 equivalent to 2 equivalents, e.g. 1.1 equivalents) in an alcohol/aqueous solvent(s) can also be employed to form the monohydrochloride salt of 5-(2,6-Di-4-morpholinyl-4-pyrimidinyl)-4-trifluoromethylpyridin-2-amine as crystalline form A. Typical elevated temperatures range from 25-80° C. Typical solvents include for example ethanol, isopropanol, and aqueous mixtures thereof. Typical concentrations of HCl used range from 0.1N to 6N HCl, including 2.25N and 4.5 N HCl.

In an exemplary embodiment, an improved process for forming the monohydrochloride salt of 5-(2,6-Di-4-morpholinyl-4-pyrimidinyl)-4-trifluoromethylpyridin-2-amine as crystalline form A was discovered, that comprises adding pyridine and 1.11 equivalent of 4.5 N HCl in isopropanol solution to 1 equivalent of 5-(2,6-Di-4-morpholinyl-4-pyrimidinyl)-4-trifluoromethylpyridin-2-amine in isopropanol solution at 60° C. Crystalline form A of the monohydrochloride salt was confirmed by XRD, the XRD as disclosed in WO PCT/US2011/053808. One advantage of the improved process is that formation of the di-hydrchloride salt of 5-(2,6-Di-4-morpholinyl-4-pyrimidinyl)-4-trifluoromethylpyridin-2-amine is prevented, which acts as an impurity to the monohydrochloride salt of 5-(2,6-Di-4-morpholinyl-4-pyrimidinyl)-4-trifluoromethylpyridin-2-amine.

The starting materials, reaction aids used in this process step are known or obtainable in analogy to known processes. Advantageously, the starting materials are obtained as described herein.

It has been found that the solid forms of the compound of Formula A and its salts surprisingly possess particularly beneficial pharmacokinetic properties that make them particularly suitable for the preparation of pharmaceutical compositions comprising the compound of Formula A and salts thereof. Distinct crystal forms have different physical properties such as melting points, hygroscopicities, solubilities, flow properties or thermodynamic stabilities, and, hence, distinct crystal forms allow the choice of the most suitable form for a certain use or aspect, e.g., the use as an intermediate in the process of drug manufacture or in distinct administration forms like tablets, capsules, ointments or solutions.

Compound A was originally described in WO2007/084786, the contents of which are incorporated herein by reference. Compound A is an inhibitor of PI3K (phosphatidylinositol 3-kinase) and modulates phosphorylation of AKT in biochemical, as well as cellular assays. Accordingly, Compound A and its pharmaceutically acceptable salts, and pharmaceutical compositions comprising Compound A or its pharmaceutically acceptable salt, can be used for the prevention, amelioration or treatment of diseases depending on PI3K. As described herein, the free base of Compound A can be a solid form that exists as one or more polymorph forms, including anhydrous and hydrates. The monohydrochloride salt of Compound A can be a solid form that exists as one or more polymorph forms, including anhydrous, hydrates and solvates. These polymorph forms (alternatively known in the art as polymorphic forms or crystal forms) differ with respect to their X-ray powder diffraction patterns, spectroscopic, physiochemical and pharmacokinetic properties, as well as their thermodynamic stability.

It has now been surprisingly found that under certain conditions new particular solid forms of Compound A, its hydrates, its salts and the hydrates or solvates of its salts may be found, which are described hereinafter, and which have advantageous utilities and properties The solid, preferably crystalline, forms of the compound of formula A, its hydrates, its salts and hydrates or solvates of its salts may preferably be used in the treatment of cellular proliferative diseases such as tumor and/or cancerous cell growth mediated by PI3K. In particular, the compounds of formula A, its hydrates, its salts and hydrates or solvates of its salts are useful in the treatment of human or animal (e.g., murine) cancers, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

In one embodiment, the invention relates to the use of polymorph Form A of 5-(2,6-Di-4-morpholinyl-4-pyrimidinyl)-4-trifluoromethylpyridin-2-amine monohydrochloride in the treatment of cancer.

EXAMPLES

The following examples illustrate the invention without limiting the scope thereof. It is understood that the invention is not limited to the embodiments set forth herein, but embraces all such forms thereof as come within the scope of the disclosure.

Example 1

Preparation of N-(5-bromo-4-(trifluoromethyl)pyridin-2-yl)acetamide

A reactor was charged with 5-bromo-4-(trifluoromethyl) pyridin-2-amine (50 g, 207.462 mmol). Ethyl acetate (50 ml) was added and the mixture was stirred for 10 minutes. Heptane (100 ml) was added. The mixture was warmed to 80° C. within 30 minutes. Acetic anhydride (27.404 ml, 290.446 mmol) was continuously added within a time period of 3 hours. The reaction mixture was stirred at 80° C. for 5 hours. Solvent was removed by distillation (80° C., 750-550 mbar) until a residual volume of 60 ml was obtained. The mixture was cooled to 0° C. Heptane (200 ml) was added and the mixture was stirred at 0° C. for 2 hours. The product was collected by filtration. The residue was washed with heptane (25 ml) and dried in a tray dryer for 16 h at 40° C., <20 mbar to yield 55.2 g (94.6%) of N-(5-bromo-4-(trifluoromethyl)pyridin-2-yl)acetamide as slightly brown solid.

Example 2

Preparation of N-(5-(1,3,6,2-dioxazaborocan-2-yl)-4-(trifluoromethyl)pyridin-2-yl)acetamide A reactor was charged with N-(5-bromo-4-(trifluoromethyl)pyridin-2-yl)acetamide (70.000 g, 247.310 mmol) and tetrahydrofuran (480.261 ml, 5861.254 mmol). The mixture was stirred for 10 minutes. The mixture was cooled to 2° C. within 30 minutes. Isopropylmagnesiumcloride lithium chloride 1.3M in THF (197.848 ml, 247.310 mmol) was continuously added within a time period of 2 hours. The mixture was warmed to 22° C. within 30 minutes. A second addition of isopropylmagnesiumcloride lithium chloride 1.3M in THF (257.203 ml, 321.503 mmol) was continuously added within a time period of 2 hours. The mixture was stirred at 22° C. for 30 minutes after addition of the Grignard reagent was complete. Triisopropyl borate (116.280 g, 618.276 mmol) was added to the stirred mixture for 1 hour. Solvent was removed by distillation (20° C., 430-80 mbar) until a residual volume of 550 ml was obtained. The solvent 2-methyltetrahydrofuran (500 ml) was added at 20° C. and the mixture was stirred. Solvent was removed by distillation at reduced pressure until a residual volume of 550 ml was obtained. An additional amount of the solvent 2-methyltetrahydrofuran (200 ml) was added at 20° C. and the mixture was stirred. The mixture was decanted and added dropwise to a second reactor charged with 70.0 g concentrated HCl (aq), 280 ml brine and 300 g water. The mixture was cooled to 7° C. and the pH of the mixture was adjusted to 2.97 by the addition of 148.1 g of 1N NaOH (aq) and warmed to 20° C. and the mixture was stirred. The pH was adjusted to 3 with the addition of another 10.8 g of 1N NaOH (aq). The organic phase was separated from the aqueous phase and 500 ml of 2-methyltetrahydrofuran was added to the organic phase. Solvent was removed by distillation at reduced pressure until a residual volume of 750 ml was obtained. The azeotropic distillation of the organic phase was performed an additional two times with 2×500 ml of 2-methyltetrahydrofuran added to the organic phase. The 750 ml mixture was filtered and added continuously to a third reactor charged with 2,2'-azanediyldiethanol (26.001 g, 247.310 mmol) and 900 ml iPrOH for 1 hour at 23° C. and the mixture was stirred. Solvent was removed by distillation at reduced pressure until a residual volume of 300 ml was obtained. An additional amount of isopropanol (900 ml) was added at 20° C. and the mixture was stirred. Solvent was removed by distillation at reduced pressure until a residual volume of 300 ml was obtained. The mixture was cooled to −10° C., and the suspended solids were collected by filtration washed with 100 ml of isopropanol at this temperature to provide 57.5 g (73.3%) of product, N-(5-(1,3,6,2-dioxazaborocan-2-yl)-4-(trifluoromethyl)pyridin-2-yl)acetamide.

Example 3

Preparation of N-(5-(2,6-dimorpholinopyrimidin-4-yl)-4(trifluoromethyl)pyridin-2-yl)acetamide N-(5-(1,3,6,2-dioxazaborocan-2-yl)-4-(trifluoromethyl) pyridin-2-yl)acetamide (25 g, 78.846 mmol) was dissolved in a mixture of dimethoxyethane (200 mL) and water (100 mL) at 2-7° C. and the solution was transferred into a jacketed, pre-cooled dropping funnel with 3° C. jacket temperature. The temperature of the dropping funnel is kept at 3° C. The compound 4,4'-(6-chloropyrimidine-2,4-diyl) dimorpholine (22.45 g, 78.843 mmol) and $K_2CO_3$ (21.8 g, 157.7 mmol) were placed in an inertized 1 L reactor and 1,2-dimethoxyethane (200 mL) was added, followed by the addition of water (25 mL). The reactor is evacuated to 100 mbar and flushed with nitrogen two times. The suspension was heated to 74-78° C. A biphasic solution was formed. The solution was stirred for additional 10 minutes under reflux and a solution of triphenylphosphine (0.822 g) in dimethoxyethane (15 mL, 3.134 mmol) was added. Stirring under reflux was continued for additional 10 minutes, after which time a solution of palladiumacetate (0.176 g, 0.784 mmol) in dimethoxyethane (15 mL) was added to the refluxing reaction mixture. The reaction mixture was stirred for additional 10 minutes under reflux. To this mixture under intense stirring, the solution of N-(5-(1,3,6,2-dioxazaborocan-2-yl)-4-(trifluoromethyl)pyridin-2-yl)acetamide was added via dropping funnel for 4.5 hours, maintaining the reaction mixture at reflux and the temperature of the dropping funnel at 3° C. Intense stirring was continued for additional 15 minutes at reflux and the temperature was cooled down to 45-60° C. Part of the solvent (270 mL) was distilled at 45-60° C./125 mbar and water (200 mL) was added in parallel. Additional solvent (100 mL) was distilled at reduced pressure and water (100 mL) was added in parallel. The suspension was cooled down to IT 25° C., stirred for 30 minutes at this temperature and the precipitate was isolated by filtration. The filter cake was washed with water (2×100 mL) and the product was dried overnight at 2 mbar/25° C. to obtain 37.3 g (quantitative yield) of N-(5-(2,6-dimorpholinopyrimidin-4-yl)-4-(trifluoromethyl)pyridin-2-yl)acetamide. The product was used as is for the next step.

In an alternative procedure, N-(5-(1,3,6,2-dioxazaborocan-2-yl)-4-(trifluoromethyl)pyridin-2-yl)acetamide; 25 g) was dissolved in a mixture of tetrahydrofuran (200 mL) and water (100 mL) at 2-5° C. and the solution was transferred into a jacketed, pre-cooled dropping funnel with 3° C. jacket temperature. The temperature of the dropping funnel was kept at approximately 3° C.

4,4'-(6-Chloropyrimidine-2,4-diyl)dimorpholine; 22.45 g) and $K_2CO_3$ (21.8 g) were placed in an inertized 1 L reactor and tetrahydrofuran (100 mL) was added, followed by the addition of water (25 mL). The biphasic mixture was stirred and heated to reflux at 80° C. (jacket temperature) under stirring. The solution thus obtained was stirred for additional 10 minutes under reflux, and a solution of triphenylphosphine (1.241 g) in tetrahydrofuran (5 mL) was added. Stirring under reflux was continued for an additional 10 minutes, after which time a solution of palladiumacetate (0.266 g) in tetrahydrofuran (5 mL) was added to the refluxing reaction mixture. Stirring was continued for additional 10 min at 80° C. (jacket temperature) under reflux. To this mixture under intense stirring, the solution of N-(5-(1,3,6,2-dioxazaborocan-2-yl)-4-(trifluoromethyl)pyridin-2-yl)acetamide was added via the dropping funnel during approximately 6 hours, maintaining the reaction mixture at reflux and the temperature of the dropping funnel at approximately 3° C. Intense stirring was continued for an additional 15 minutes under reflux and the temperature was cooled down to 65-70° C. (jacket temperature). Isopropanol (60 mL) was added to the reaction mixture, followed by the addition of water (100 mL). Part of the solvent (approximately 170 mL) was distilled off at 70° C. (jacket temperature) under reduced pressure starting at 800 mbar until approximately 400 mbar. Water (100 mL) was added to the mixture and another portion of solvent (approximately 100 mL) was distilled off at 70° C. (jacket temperature) under reduced pressure until approximately 400 mbar. The suspension thus obtained was cooled to 25° C. and stirred for 1 hour at this temperature. The product was isolated by filtration and the filter-cake was washed with water (100 mL). The product was dried over night at 50° C. and 30 mbar to obtain N-(5-(2,6-dimorpholinopyrimidin-4-yl)-4-(trifluoromethyl)pyridin-2-yl)acetamide (34.39 g; 96.4% crude yield). The crude product was used as is for the next step.

Example 4

Preparation of 5-(2,6-Di-4-morpholinyl-4-pyrimidin-4-yl)-4(trifluoromethyl)pyridin-2-amine (Compound A)

N-(5-(2,6-dimorpholinopyrimidin-4-yl)-4-(trifluoromethyl)pyridin-2-yl)acetamide (36.1 g, 76.52 mmol) was suspended in demineralized water (180 mL). The suspension was treated with aqueous 2N HCl (180 mL) and the mixture was heated to 70° C.-75° C. The reaction mixture was stirred at 75° C. for 3 hours at this temperature. The reaction mixture was then cooled down to 25° C. and clear filtered. The filter cake is washed with water (2×50 mL). Isopropylacetate (IPA, 100 mL) was added to the filtrate and the pH of the biphasic solution was adjusted to 1.75 by slow addition of aq. 2N NaOH (105 g) under intense stirring. Stirring was continued for additional 15 minutes at 20-25° C. and the phases were separated. The aqueous phase was extracted with additional IPA (2×50 mL) and the phases were separated. The pH of the aqueous phase was adjusted to 9.1 by slow addition of 2N NaOH (114 g). A suspension was formed. Isopropylacetate (400 mL) was added to the suspension and the mixture was heated to 40° C. under stirring to obtain a biphasic solution. The phases were separated and the water phase was extracted again with isopropylacetate (50 mL). The organic phases were combined. An aqueous solution of N-Acetyl-L-cysteine (140 mL) was added to the organic phase and the mixture was stirred at 50° C. for 1 hour. The phases were separated. The organic phase was treated again with an aqueous solution of N-Acetyl-L-cysteine (140 mL) for additional 1 hour at 60° C. and the phases are separated. Finally, the organic phase was washed with demineralized water (70 mL) and the temperature was cooled down to 20° C. Aqueous 1N HCl solution (200 mL) was added slowly to the organic phase, maintaining the temperature at 20-25° C. The mixture was intensively stirred for 10 minutes and the phases were separated. The organic phase was extracted again with aqueous 1N HCl solution (50 mL) and with water (50 mL). The aqueous HCl and water phases were clear filtered and combined. The pH of the combined aqueous phase was adjusted to 7.1 by slow addition of aqueous 2N NaOH solution (123 g) and the formed suspension was stirred for at least 3 hours at 20-25° C. The product was isolated by filtration and the filter cake was washed with demineralized water (3×100 mL). The product was dried in vacuo at 50° C. over night to obtain 5-(2,6-Di-4-morpholinyl-4-pyrimidin-4-yl)-4-(trifluoromethyl)pyridin-2-amine (>99.5 a % purity as determined by HPLC) and 85% overall yield.

Preparation of the N-Acetyl-L-cystein Solution:

N-Acetyl-L-cystein (30.6 g) was dissolved in demineralized water (300 mL) and aqueous 4N NaOH solution (46.8 g) was added dropwise until a pH of 7.0 is achieved. 70 mL of this solution is diluted with 210 mL of demineralized water and the solution was used for the extractions described above.

Example 5

5-(2,6-Di-4-morpholinyl-4-pyrimidinyl)-4-(trifluoromethyl)pyridin-2-amine monohydrochloride In a nitrogen-flushed 3 L reactor that equipped with an overhead stirrer, condenser, nitrogen inlet/outlet and 500 mL addition funnel, 10.5 g (25.59 mmol, 1 eq.) of 5-(2,6-Di-4-morpholinyl-4-pyrimidin-4-yl)-4-(trifluoromethyl)pyridin-2-amine was suspended in isopropanol (79.0 g), water and pyridine (0.2 g) mixture (97:2.5:0.3 w/w/w) at room temperature. The suspension was heated to 70° C. and a slightly turbid solution was obtained. The turbid solution was filtered at 70° C. The clear solution was cooled to 60° C. and a first portion (1.03 ml, 4.39 mmol, 0.2 eq.) of 4.5 N HCl in isopropanol was added. The still clear solution was cooled to 55° C., seeded with 0.19 g of Form A of the monohydrochloride salt of compound A suspended in an isopropanol: water (97:2.5 w/w) mixture and stirred for 15 minutes. A second portion (4.67 ml, 19.94 mmol, 0.91 eq.) of 4.5 N HCl in isopropanol was added very slowly. The suspension was stirred for 60 minutes and cooled down to −10° C. in 16 hours and stirred for another 60 min at −10° C. The solid product was isolated by filtration and washed three times with pre-cooled isopropanol (3×18 g). The solid product was dried at 90° C. under vacuum for at least 24 hours to afford 8.64 g (88.2% yield) of 5-(2,6-Di-4-morpholinyl-4-pyrimidinyl)-4-(trifluoromethyl)pyridine-2-amine monohydrochloride as a yellow, crystalline solid, polymorph Form A.

Other monohydrochloride salt forming experiments that produce the crystalline form A monohydrochloride salt are summarized below:

Experiments with Pyridine Hydrochloride

| Solvents | Solvent Composition | Pyridine Hydrochloride range |
|---|---|---|
| Ethanol:Isopropanol:Water | 65:32:2 (m:m:m) | 1.1-1.15 eq |
| Ethyl acetate | | 2 eq |

Experiments with Pyridine

| Solvents | Solvent Composition | Pyridine | HCl in Isopropanol |
|---|---|---|---|
| Ethanol:Iso-propanol:Water | 68:32:2 (m:m:m) | 0.23eq 0.08-1.15eq 0.11 eq | 0.95 1.11 eq 1.54eq |
| Isopropanol:Water | 75:2 (m:m) | 0.115-0.37eq | 0.94-1.28eq |
| Isopropanol:Water | 75:2 (m:m) | 0.115-0.37eq | 0.94-1.28eq |
| Isopropanol | 64.3:2.5 (m:m) | 0.115 | 1.11eq |

Example 6

Preparation of N-(5-(1,3,6,2-dioxazaborocan-2-yl)-4-(trifluoromethyl)pyridin-2-yl)amine A reactor was charged with 5-bromo-4-(trifluoromethyl)pyridin-2-amine (10.000 g, 41.49 mmol) and tetrahydrofuran (44 ml). The mixture was stirred. The mixture was cooled to 0° C. Four equivalents of isopropylmagnesiumcloride lithium chloride 1.3M in THF (121.4 g, 165.97 mmol) was continuously added within a time period of 45 min maintaining the temperature at <10° C. The mixture was warmed to 44° C. after addition of the Grignard reagent was complete and stirred for 4.5 h at this temperature. Triisopropyl borate (31.85 g, 165.97 mmol) in tetrahydrofuran (32 mL) was added to the stirred mixture within 15 min and the mixture was stirred for additional 30 min at 44° C. The mixture was cooled to 0° C. To the mixture was added dropwise 5 N HCl (30.18 mL; 165.97 mmol) in isopropanol. The mixture was warmed to 22° C. and stirred over night. The formed solid was removed by filtration, the filter cake was washed with 50 mL of tetrahydrofuran and was disposed. To the filtrate was added slowly over 45 min a solution of diethanolamine (13.22 g) in tetrahydrofuran (95 mL). The formed suspension was stirred 30 min and the solid was removed by filtration. The filter cake was washed with tetrahydrofuran (50 mL) and disposed. The filtrate was diluted with isopropylacetate (100 mL) and the solvent was partly evaporated to a final volume of ca. 80 mL. The solution was diluted with additional isopropylacetate (20 mL) and saturated aq. NaCl was added (100 mL). The pH of the aqueous phase was adjusted to 5-6 with 2M HCl and water (25 mL) was added to the biphasic mixture. The phases were separated and the organic phase was washed again with sat. aq. NaCl-solution. The aqueous phases were re-extracted with isopropylacetate (100 mL) and the organic phases were combined. To the organic phase was added a solution of diethanolamine (4.4 g) in tetrahydrofuran (44 mL) within 30 min. The solvent was partly evaporated under reduced pressure at 35-40° C. to a final volume of ca. 100 mL. The formed suspension was stirred for 30 min at room temperature and the product was isolated by filtration. The filter cake was washed with isopropylacetate (50 mL) and dried in vacuo at room temperature to obtain 8.73 g (76.5%) of product, N-(5-(1,3,6,2-dioxazaborocan-2-yl)-4-(trifluoromethyl)pyridin-2-yl)amine.

Example 7

Preparation of 5-(2,6-Di-4-morpholinyl-4-pyrimidin-4-yl)-4-(trifluoromethyl)pyridin-2-amine (Compound A)

The compound 4,4'-(6-chloropyrimidine-2,4-diyl)dimorpholine (2.85 g, 9.99 mmol) and K₂CO₃ (2.76 g, 19.97 mmol) were placed in an inertized 1 L reactor and 1,2-dimethoxyethane (100 mL) was added, followed by the addition of water (25 mL). The reactor was evacuated to 100 mbar and flushed with nitrogen two times. The suspension was heated to 60° C. A solution of 0.1 g tetrakistriphenylphosphinepalladium in 2 mL dimethoxyethane (0.100 g, 0.087 mmol) was added. The suspension was heated to 78° C. and stirred for three hours. N-(5-(1,3,6,2-dioxazaborocan-2-yl)-4-(trifluoromethyl)pyridin-2-yl)amine (2.75 g, 9.99 mmol) was dissolved in a mixture of dimethoxyethane (20 mL) and 200 mL water. The reaction mixture was stirred for additional 10 minutes under reflux at 95° C. The suspension was cooled down to 25° C. and stirred for 30 minutes at this temperature. The product was isolated by filtration and the filter cake was washed with demineralized water (3×100 mL). The product was 5-(2,6-Di-4-morpholinyl-4-pyrimidin-4-yl)-4-(trifluoromethyl)pyridin-2-amine, as determined by HPLC.

Example 8

Preparation of Trianion of 5-bromo-4-(trifluoromethyl)pyridin-2-amine Using 3.5 Equivalents of Isopropylmagnesium Chloride, Lithium Chloride Complex

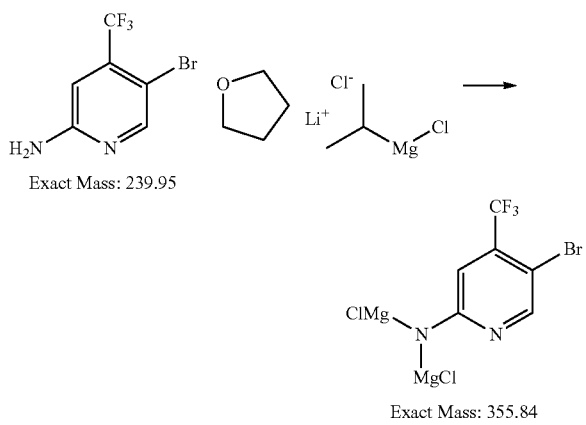

Exact Mass: 239.95

Exact Mass: 355.84

A reactor was charged with 5-bromo-4-(trifluoromethyl)pyridin-2-amine (1.000 g, 4.149 mmol) and tetrahydrofuran (7.72 ml). The mixture was stirred for 10 minutes. The mixture was cooled to 0° C. within 30 minutes. Isopropylmagnesiumcloride lithium chloride 1.3M in THF (6.383 ml, 8.298 mmol) was continuously added within a time period of 1.5 hours at 0° C. An additional 1.5 equivalents of isopropylmagnesiumcloride lithium chloride 1.3M in THF (4.788 ml, 6.224 mmol) was continuously added within a time period of 1.5 hours at 0° C. An additional 0.5 equivalents of isopropylmagnesiumcloride lithium chloride 1.3M in THF (1.596 ml, 2.075 mmol) was continuously added within a time period of 1 hour at 0° C. The product was the trianion of 5-bromo-4-(trifluoromethyl)pyridin-2-amine, as determined by HPLC and LCMS.

Example 9

Preparation of 5-(2,6-Di-4-morpholinyl-4-pyrimidin-4-yl)-4-(trifluoromethyl)pyridin-2-amine (Compound A)

The compound 4,4'-(6-chloropyrimidine-2,4-diyl)dimorpholine (0.40 g, 1.405 mmol), 1,1'-Bis(diphenylphosphino)ferrocene (0.040 g, 0.070 mmol) and Palladium acetate (0.016 g, 0.070 mmol) and 2 mL of tetrahydrofuran were placed in an inertized reactor. The reactor is evacuated to 100 mbar and flushed with nitrogen two times. Isopropylmagnesiumcloride lithium chloride 1.3M in THF (1.405 mmol) was added at 30° C. followed by an equivalent amount of the trianion of 5-bromo-4-(trifluoromethyl)pyridin-2-amine (1.405 mmol). The suspension was stirred for 0.5 hours. The product was 5-(2,6-Di-4-morpholinyl-4-pyrimidin-4-yl)-4-(trifluoromethyl)pyridin-2-amine, as determined by HPLC and LCMS.

Example 10

Preparation of the Dianion of N-(5-bromo-4-(trifluoromethyl)pyridin-2-yl)acetamide Using 2.5 Equivalents of Isopropylmagnesium Chloride, Lithium Chloride Complex A reactor was charged with N-(5-bromo-4-(trifluoromethyl)pyridin-2-yl)acetamide (1.405 mmol) and tetrahydrofuran (2 mL). The mixture was stirred for 10 minutes. The mixture was cooled to 0° C. within 30 minutes. Isopropylmagnesiumcloride lithium chloride 1.3M in THF (ml, 1.405 mmol) was continuously added within a time period of 1 hour at 0° C. An additional 1.5 equivalents of isopropylmagnesiumcloride lithium chloride 1.3M in THF (4.788 ml, 2.107 mmol) was continuously added within a time period of 1.5 hours at 0° C. The product was the dianion of N-(5-bromo-4-(trifluoromethyl)pyridin-2-yl)acetamide, as determined by HPLC and LCMS.

Example 11

Preparation of N-(5-(2,6-dimorpholinopyrimidin-4-yl)-4-(trifluoromethyl)pyridin-2-yl)acetamide The compound 4,4'-(6-chloropyrimidine-2,4-diyl)dimorpholine (0.40 g, 1.405 mmol), 1,1'-Bis(diphenylphosphino)ferrocene (0.040 g, 0.070 mmol) and Palladium acetate (0.016 g, 0.070 mmol) and 2 mL of tetrahydrofuran were placed in an inertized reactor. The reactor is evacuated to 100 mbar and flushed with nitrogen two times. Isopropylmagnesiumcloride lithium chloride 1.3M in THF (1.405 mmol) was added at 30° C. followed by an equivalent amount of the dianion of N-(5-bromo-4-(trifluoromethyl)pyridin-2-yl)acetamide (1.405 mmol) and 1-iodoadamantane (0.413 g, 1.405 mmol). The suspension was stirred for 0.5 hours. The product was N-(5-(2,6-dimorpholinopyrimidin-4-yl)-4-(trifluoromethyl)pyridin-2-yl)acetamide as determined by HPLC and LCMS.

Example 12

Preparation of N-(5-(2,6-dimorpholinopyrimidin-4-yl)-4-(trifluoromethyl)pyridin-2-yl)acetamide The compound 4,4'-(6-chloropyrimidine-2,4-diyl)dimorpholine (0.40 g, 1.405 mmol), NiCl₂(dppf) 1,1'-Bis(diphenylphosphino)ferrocene (0.048 g, 0.070 mmol) and 2 mL of tetrahydrofuran were placed in an inertized reactor. The reactor is evacuated to 100 mbar and flushed with nitrogen two times. Isopropylmagnesiumcloride lithium chloride 1.3M in THF (1.405 mmol) was added at 30° C. followed by an equivalent amount of the dianion of N-(5-bromo-4-(trifluoromethyl)pyridin-2-yl)acetamide (1.405 mmol). The suspension was stirred for 0.5 hours. The product was N-(5-(2,6-dimorpholinopyrimidin-4-yl)-4-(trifluoromethyl)pyridin-2-yl)acetamide as determined by HPLC and LCMS.

The invention claimed is:
1. A process for manufacturing a compound of formula A

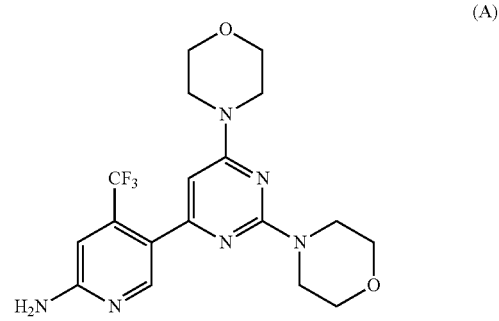 [SMILES: Nc1cc(C(F)(F)F)c(-c2cc(N3CCOCC3)nc(N3CCOCC3)n2)cn1]

(A)

comprising the steps of:
(a) acylating 5-bromo-4-(trifluoromethyl)pyridin-2-amine in a reaction mixture comprising solvents ethyl acetate and heptane, and the acid anhydride acetic anhydride to form N-(5-bromo-4-(trifluoromethyl)pyridin-2-yl)acetamide;
(b) reacting N-(5-bromo-4-(trifluoromethyl)pyridin-2-yl)acetamide with an alkyl Grignard reagent isopropylmagnesium chloride lithium chloride in the solvent tetrahydrofuran followed by an triaklylborate triisopropylborate and 2,2'-azanediyldiethanol in one or more solvents selected from 2-methyltetrahydrofuran or isopropanol to form the boronic ester product, N-(5-(1,3,6,2-dioxazaborocan-2-yl)-4-(trifluoromethyl)pyridin-2-yl)acetamide, having the structure

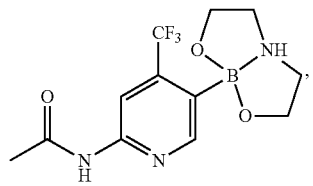

wherein the Boron to Nitrogen bond is a coordinative bond;
(c) coupling the boronic ester product, N-(5-(1,3,6,2-dioxazaborocan-2-yl)-4-(trifluoromethyl)pyridin-2-yl)

acetamide, with 4,4'-(6-Chloropyrimidine-2,4-diyl)di[morpholine] via a palladium catalyzed Suzuki coupling reaction comprising (i.) a catalyst comprising triphenylphosphine and one or more solvents selected from dimethoxyethane, tetrahydrofuran or water, with Pd(OAc)$_2$, and (ii.) a base potassium carbonate to form N-(5-(2,6-dimorpholinopyrimidin-4-yl)-4-(trifluoromethyl)pyridin-2-yl)acetamide; and (d) hydrolyzing N-(5-(2,6-dimorpholinopyrimidin-4-yl)-4-(trifluoromethyl)pyridin-2-yl)acetamide in one or more solvents selected from isopropylacetate or water under acidic conditions to form the compound of formula A.

2. The process of claim 1, wherein the palladium catalysed Suzuki coupling of step (c) comprises generating the palladium catalyst in-situ from palladium acetate and triphenylphosphine in an organic solvent selected from dimethoxyethane, tetrahydrofuran or water.

3. The process of claim 1, wherein the hydrolysed N-(5-(2,6-dimorpholinopyrimidin-4-yl)-4-(trifluoromethyl)pyridin-2-yl)acetamide is treated with N-Acetyl-L-cysteine.

* * * * *